United States Patent
Fukuda et al.

(10) Patent No.: US 9,746,461 B2
(45) Date of Patent: Aug. 29, 2017

(54) URINE SAMPLE ANALYZER AND SAMPLE ANALYZING METHOD

(71) Applicant: Sysmex Corporation, Hyogo (JP)

(72) Inventors: Masakazu Fukuda, Hyogo (JP); Masamichi Tanaka, Hyogo (JP)

(73) Assignee: SYSMEX CORPORATION, Kobe (JP)

( * ) Notice: Subject to any disclaimer, the term of this patent is extended or adjusted under 35 U.S.C. 154(b) by 685 days.

(21) Appl. No.: 14/193,015

(22) Filed: Feb. 28, 2014

(65) Prior Publication Data

US 2014/0242633 A1 Aug. 28, 2014

(30) Foreign Application Priority Data

Feb. 28, 2013 (JP) .................. 2013-039746

(51) Int. Cl.
| | |
|---|---|
| G01N 33/50 | (2006.01) |
| C12Q 1/06 | (2006.01) |
| G01N 33/80 | (2006.01) |
| G01N 33/493 | (2006.01) |
| G01N 15/14 | (2006.01) |

(52) U.S. Cl.
CPC .......... *G01N 33/5094* (2013.01); *C12Q 1/06* (2013.01); *G01N 15/1425* (2013.01); *G01N 33/493* (2013.01); *G01N 33/80* (2013.01)

(58) Field of Classification Search
None
See application file for complete search history.

(56) References Cited

U.S. PATENT DOCUMENTS

| | | | |
|---|---|---|---|
| 8,440,140 B2 | 5/2013 | Nagai et al. | |
| 8,501,482 B2 | 8/2013 | Tanaka et al. | |
| 2009/0050821 A1 * | 2/2009 | Tanaka | G01N 15/1459 250/458.1 |

FOREIGN PATENT DOCUMENTS

| | | |
|---|---|---|
| CN | 101173888 A | 5/2008 |
| CN | 101236194 A | 8/2008 |
| EP | 1 136 563 A2 | 9/2001 |
| EP | 1 813 942 A1 | 8/2007 |
| EP | 1 857 804 A2 | 11/2007 |
| EP | 1 953 527 A2 | 8/2008 |
| JP | 04-337459 A | 11/1992 |
| JP | 2007-309728 A | 11/2007 |
| JP | 2008-209386 A | 9/2008 |

* cited by examiner

*Primary Examiner* — Jason Sims
(74) *Attorney, Agent, or Firm* — Brinks Gilson & Lione

(57) ABSTRACT

A urine analyzer capable of operating in a urine measurement mode and a body fluid measurement mode, the urine analyzer includes a specimen preparing section configured to prepare a measurement specimen and a detecting section configured to derive signals of particles in the measurement specimen supplied from the specimen preparing section. A computer and a memory including programs on a computer-readable medium that enable the computer to execute operations to control the specimen preparing section and the detecting section in the urine measurement mode and in the body fluid measurement mode.

13 Claims, 21 Drawing Sheets

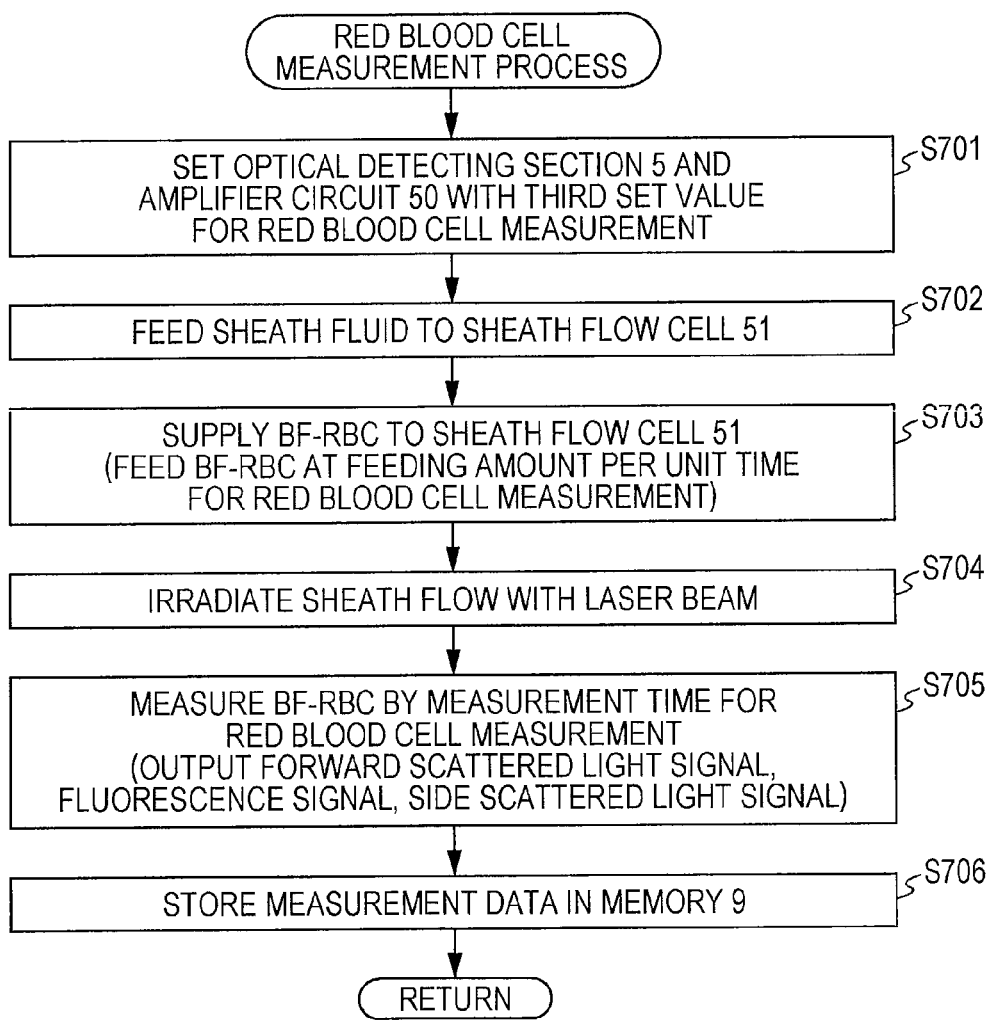

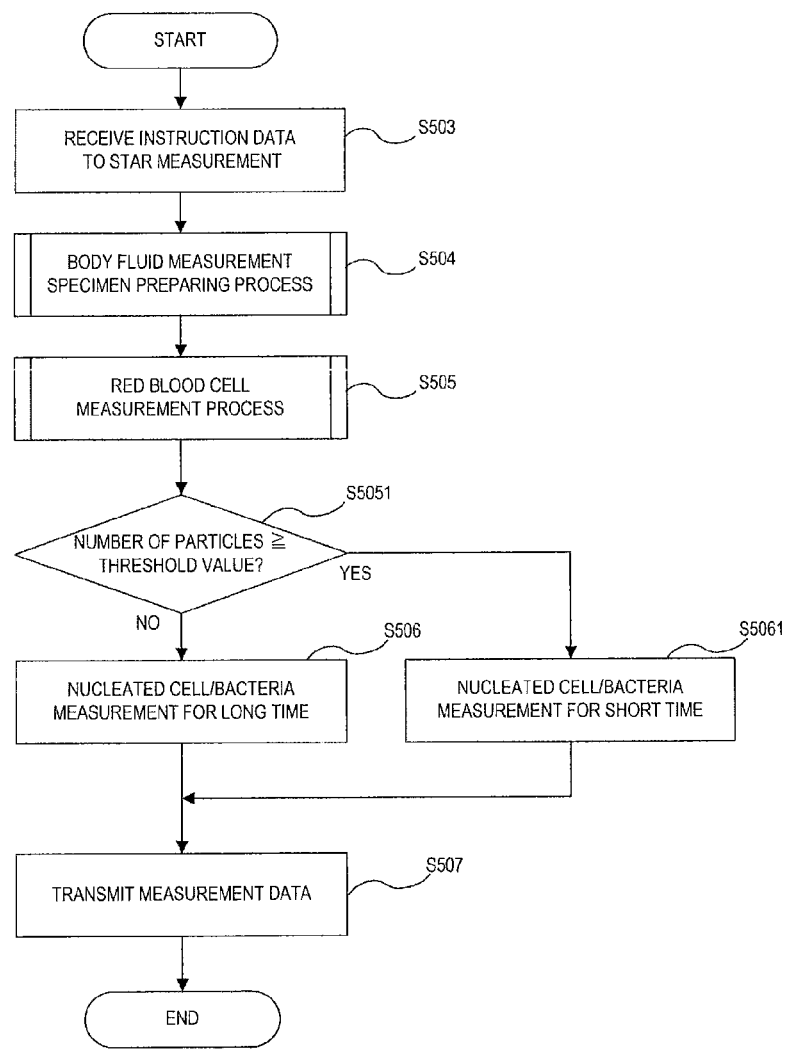

URINE SAMPLE ANALYZER AND SAMPLE ANALYZING METHOD

RELATED APPLICATIONS

This application claims the benefit of Japanese Patent Application No. JP2013-039746 filed Feb. 28, 2013, the entire disclosure of which is incorporated herein.

FIELD OF THE INVENTION

The present invention relates to a urine sample analyzer and a sample analyzing method for analyzing a sample by measuring a measurement specimen prepared from a sample and a reagent.

BACKGROUND

Sample analysis for analyzing components contained in a sample such as blood, urine, or the like collected from a living body is widely carried out in the field of clinical examinations. Sample analyzers for automatically carrying out the sample analyses are in widespread use in recent years.

U.S. Pat. No. 8,501,482 discloses a urine sediment analyzer for measuring particles in urine. In the urine sediment analyzer described in U.S. Pat. No. 8,501,482, aspirated urine sample is divided into two aliquots. One aliquot is mixed with a diluent and a first dye to prepare a measurement specimen for measuring large urine sediment such as red blood cells, white blood cells, epidermal cells, casts, and the like. Red blood cells, white blood cells, epidermal cells, casts, and the like are analyzed by optically measuring the measurement specimen. On the other hand, the other aliquot is mixed with diluent and a second dye to prepare a measurement specimen for measuring bacteria which are smaller particles than the above mentioned urine sediments. Bacteria are analyzed by optically measuring the measurement specimen.

U.S. Pat. No. 8,440,140 discloses a blood analyzer enabled to measure a body fluid.

In many medical institutions, several examination rooms are arranged according to types of samples such as a general examination room for examining urine, feces, and the like, a blood examination room for examining blood, and the like. Body cavity fluid (hereinafter referred to as "body fluid") existing in body cavity of living body is often collected and examined in the general examination room for examining urine. However, conventional urine analyzer can analyze only urine. Therefore, in order to analyze a body fluid with the conventional analyzer, an analyzer dedicated for body fluid needs to be installed in the general examination room or a body fluid analyzer in another examination room needs to be used to analyze the body fluid.

BRIEF SUMMARY

A first aspect of the disclosed subject matter is a urine analyzer capable of operating in a urine measurement mode and a body fluid measurement mode, the urine analyzer comprising: a specimen preparing section configured to prepare a measurement specimen; a detecting section configured to derive signals of particles in the measurement specimen supplied from the specimen preparing section; and a computer and a memory including programs on a computer-readable medium that enable the computer to execute operations comprising, (A) in the urine measurement mode, control the specimen preparing section to prepare a first measurement specimen by mixing a first aliquot of a urine sample and a first reagent, to prepare a second measurement specimen by mixing a second aliquot of the urine sample and a second reagent having a hemolytic effect, and to supply the first and second measurement specimens to the detecting section; and analyze the signals of the first measurement specimen to measure red blood cells in the urine sample and analyze the signals of the second measurement specimen to measure bacteria in the urine sample, (B) in the body fluid measurement mode, control the specimen preparing section to prepare a third measurement specimen by mixing a first aliquot of body fluid sample and the first reagent, to prepare a fourth measurement specimen by mixing a second aliquot of body fluid sample and the second reagent, and to supply the third and fourth measurement specimens to the detecting section; and analyze the signals of the third measurement specimen to measure red blood cells in the body fluid sample and analyze the signals of the fourth measurement specimen to measure white blood cells in the body fluid sample.

A second aspect of the disclosed subject matter is a urine analyzer capable of operating in a urine measurement mode and a body fluid measurement mode, the urine analyzer comprising: a specimen preparing section configured to prepare a mixture of sample and reagent; a detecting section configured to derive signals from the mixture supplied from the specimen preparing section; and a computer and a memory including programs on a computer-readable medium that enable the computer to execute operations comprising, in the urine measurement mode, control the specimen preparing section to prepare a first mixture of a urine sample and a first reagent, and to supply the first mixture to the detecting section according to a first measurement condition, and in the body fluid measurement mode, control the specimen preparing section to prepare a second mixture of a body fluid sample and the first reagent, and to supply the second mixture to the detecting section according to a second measurement condition different from the first measurement condition.

A third aspect of the disclosed subject matter is a method for analyzing body fluid using an automated urine analyzer, the method comprising the steps of: mixing a body fluid sample and a first reagent by the urine analyzer; mixing the body fluid sample and a second reagent having hemolytic effect by the urine analyzer; measuring red blood cells in the body fluid sample from a mixture of the body fluid sample and the first reagent by the urine analyzer; and measuring white blood cells in the body fluid sample from a mixture of the body fluid sample and the second reagent by the urine analyzer; wherein the first reagent is used to measures red blood cells in urine, and the second reagent is used to measures bacteria in urine.

BRIEF DESCRIPTION OF THE DRAWINGS

FIG. 16 is a flowchart illustrating a procedure of a measurement process of red blood cells in the body fluid;

FIG. 22 illustrates a modification of the flowchart of the measurement unit side in FIG. 14.

DETAILED DESCRIPTION

A preferred embodiment of the disclosed subject matter will be hereinafter described with reference to the drawings.

<Configuration of Urine Sample Analyzer>

In the present embodiment, a urine sample analyzer for analyzing cells in urine and cells in body fluid will be described. The urine sample analyzer of the present embodiment can operate in urine measurement mode and body fluid measurement mode. If the urine measurement mode is set, the sample analyzer retrieves the urine sample inside, and analyzes urine sediments, formed elements not containing bacteria, such as red blood cells, white blood cells, epidermal cells, casts, etc. The analyzer also analyzes bacteria in the urine. If the body fluid measurement mode is set, the sample analyzer retrieves the body fluid sample inside, and analyzes formed elements, e.g. red blood cells, white blood cells, large cells, etc. in the body fluid sample. The "body fluid" referred to herein refers to the body cavity fluid that does not include blood, urine, and lymph fluid, and that exists in the body cavity of the living body, and includes spinal fluid, cerebrospinal fluid (CSF), pleural effusion, ascites, pericarditis, joint fluid, synovial fluid, eye chamber fluid, aqueous fluid, and the like.

Figure 1:
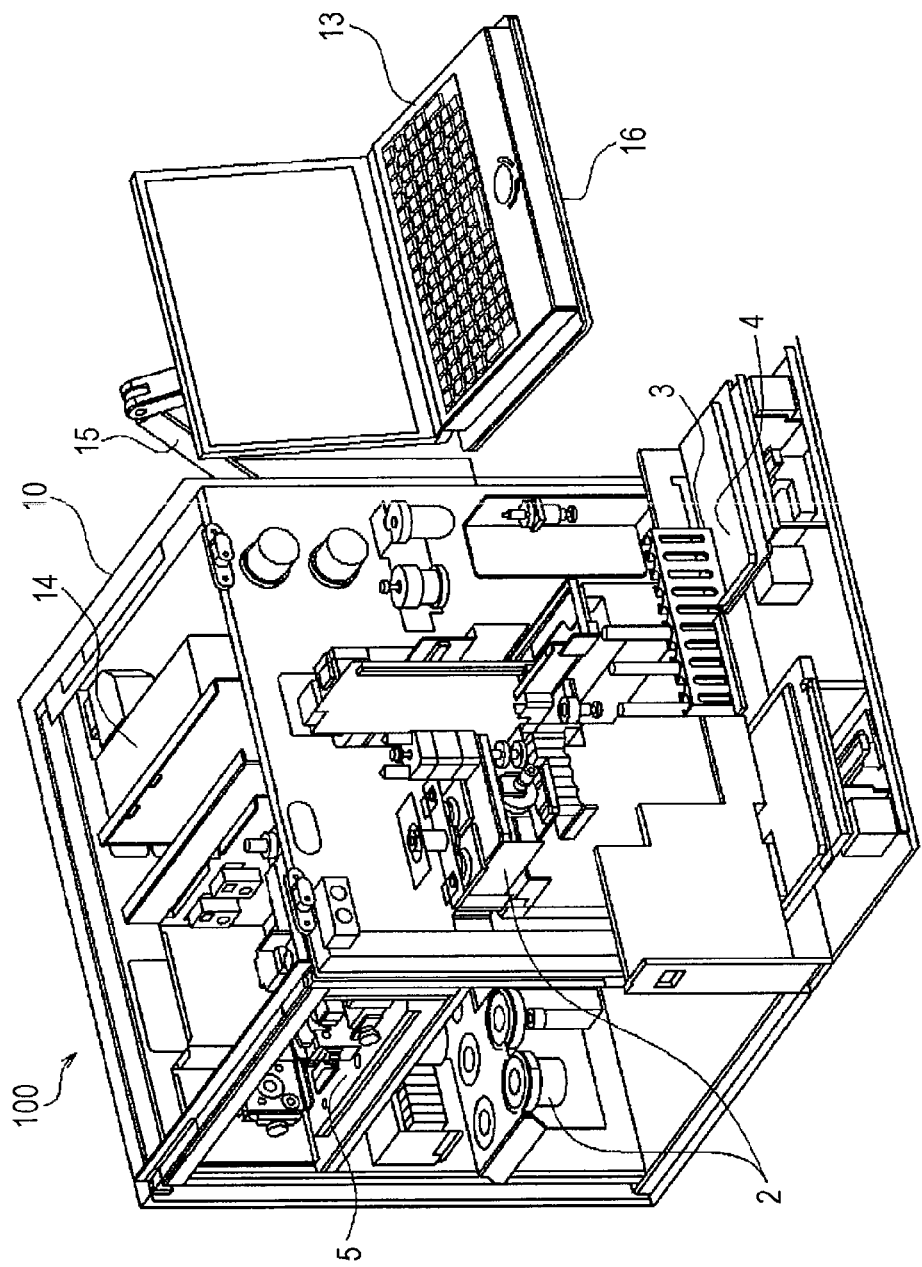
FIG. 1 is a perspective view illustrating an overall configuration of a urine sample analyzer according to an embodiment.

FIG. 1 is an outer appearance perspective view illustrating a configuration of the urine sample analyzer of the present embodiment. In FIG. 1, a urine sample analyzer 100 includes a measurement unit 10 and an information processing unit 13. The measurement unit 10 includes a specimen preparing section 2 for preparing a measurement specimen, a rack table 4 for transferring a sample rack 3, a FCM section 5 for detecting signals of cells in the measurement specimen, and a circuit section 14. A supporting board 16 is attached to a side surface of a housing by way of an arm 15, and the information processing unit 13 is installed thereon. The information processing unit 13 is data communicably connected to the circuit section 14 of the measurement unit 10.

Figure 2:
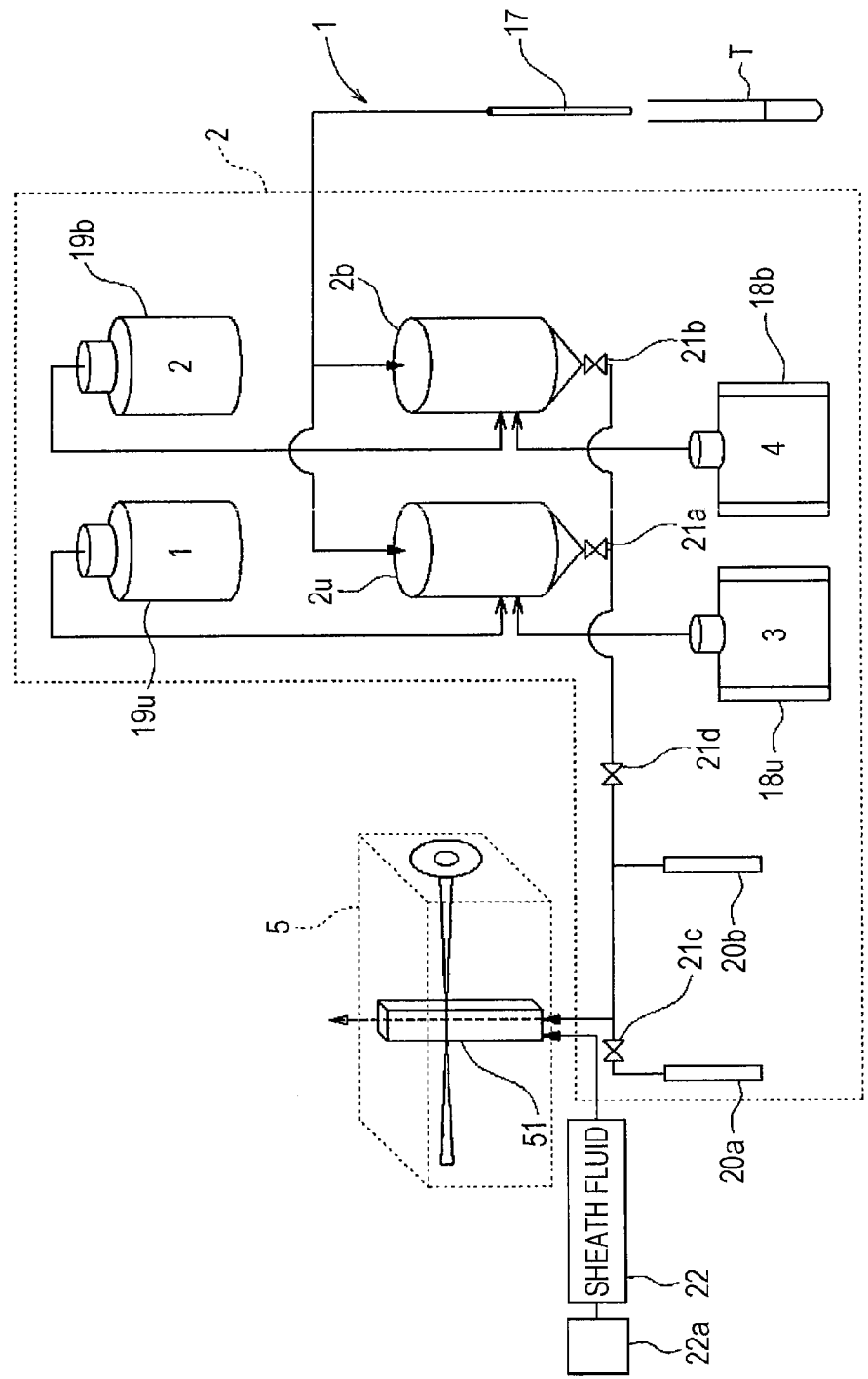
FIG. 2 is a schematic diagram of a specimen preparing section and a FCM section.

FIG. 2 is a schematic diagram of the specimen preparing section 2 and the FCM (flow cytometer) section 5. A sample distributing section 1 includes an aspirating tube 17 and a syringe pump (not shown). The sample distributing section 17 aspirates the urine or body fluid sample in a test tube T through the aspirating tube 17, and dispenses the sample into the specimen preparing section 2. The specimen preparing section 2 includes a reaction chamber 2u and a reaction chamber 2b. The sample distributing section 1 quantitatively distributes aliquots to each of the reaction chamber 2u and the reaction chamber 2b.

In the reaction chamber 2u, the distributed aliquot is mixed with a first reagent 19u serving as diluent and a third reagent 18u containing dye. Cells in the sample are stained with the dye of the third reagent 18u. In the urine measurement mode, the specimen prepared in the reaction chamber 2u is used as a measurement specimen for analyzing urine sediments such as red blood cells, white blood cells, epidermal cells, casts, and the like, relatively larger than bacteria. The measurement specimen used to measure the sediments in urine is hereinafter referred to as "U-SED". In the body fluid measurement mode, the specimen prepared in the reaction chamber 2u is used as a measurement specimen for analyzing red blood cells in the body fluid. The measurement specimen used to analyze the red blood cells in the body fluid is hereinafter referred to as "BF-RBC".

In the reaction chamber 2b, on the other hand, the distributed aliquot is mixed with a second reagent 19b serving as diluent and a fourth reagent 18b containing dye. As will be described later, the second reagent 19b has an ability of hemolysis. Cells in the sample are stained with the dye of the fourth reagent 18b. In the urine measurement mode, the specimen prepared in the reaction chamber 2b serves as the measurement specimen for analyzing bacteria in urine. The measurement specimen used to measure bacteria in urine is hereinafter referred to as "U-BAC". In the body fluid measurement mode, the specimen prepared in the reaction chamber 2b serve as the measurement specimen for analyzing nucleated cells such as white blood cells, large cells, and bacteria in body fluid. The measurement specimen used to analyze the nucleated cells in body fluid is hereinafter referred to as "BF-WBC". As examples of the "large cells", the cells stripped from the body cavity inner membrane or from the visceral abdomen membrane and having larger size than white blood cells such as mesothelial cells, histocytes (macrophages), and the like can be mentioned.

A tube is extended from the reaction chamber 2u to a sheath flow cell 51 of the FCM section 5, so that the measurement specimen prepared in the reaction chamber 2u can be supplied to the sheath flow cell 51. An electromagnetic valve 21a is arranged at the outlet of the reaction chamber 2u. A tube is also extended from the reaction chamber 2b. The tube is coupled to the middle of the tube extending from the reaction chamber 2u. Thus, the measurement specimen prepared in the reaction chamber 2b can be supplied to the sheath flow cell 51. An electromagnetic valve 21b is also arranged at the outlet of the reaction chamber 2u.

The coupled tube extended from the reaction chambers 2u, 2b to the sheath flow cell 51 is branched short of the sheath flow cell 51, and the branched tube is connected to a syringe pump 20a. An electromagnetic valve 21c is arranged between the syringe pump 20a and a branched point.

The tube is further branched in the middle from the connecting point of the tubes extended from the reaction chambers 2u, 2b to the branched point, and the branch destination is connected to a syringe pump 20b. An electromagnetic valve 21d is arranged between the branched point of the tube extending to the syringe pump 20b and the connecting point.

The specimen preparing section 2 includes a sheath fluid accommodating portion 22 that accommodates the sheath fluid, the sheath fluid accommodating portion 22 being connected to the sheath flow cell 51 by a tube. A compressor 22a is connected to the sheath fluid accommodating portion 22. When the compressor 22a is driven, compressed air is supplied to the sheath fluid accommodating portion 22 so that the sheath fluid is supplied from the sheath fluid accommodating portion 22 to the sheath flow cell 51.

In the two types of measurement specimens in reaction chambers 2u, 2b, the measurement specimen in the reaction chamber 2u is first supplied to the FCM section 5. That is, in the urine measurement mode, U-SED is first supplied. In the body fluid measurement mode, BF-RBC is first supplied. A narrow flow enveloped with the sheath fluid is formed in the sheath flow cell 51, and the laser light is irradiated thereon. Similarly thereafter, the measurement specimen of the reaction chamber 2b is supplied to the FCM section 5. That is, in the urine measurement mode, U-BAC is first supplied. In the body fluid measurement mode, BF-WBC is first supplied. A narrow flow is formed in the sheath flow cell 51, and the laser light is irradiated thereon. Such operation is automatically carried out by operating the electromagnetic valves 21a, 21b, 21c, 21d, and drive units (not shown) according to the control of the microcomputer 11.

Figure 3:
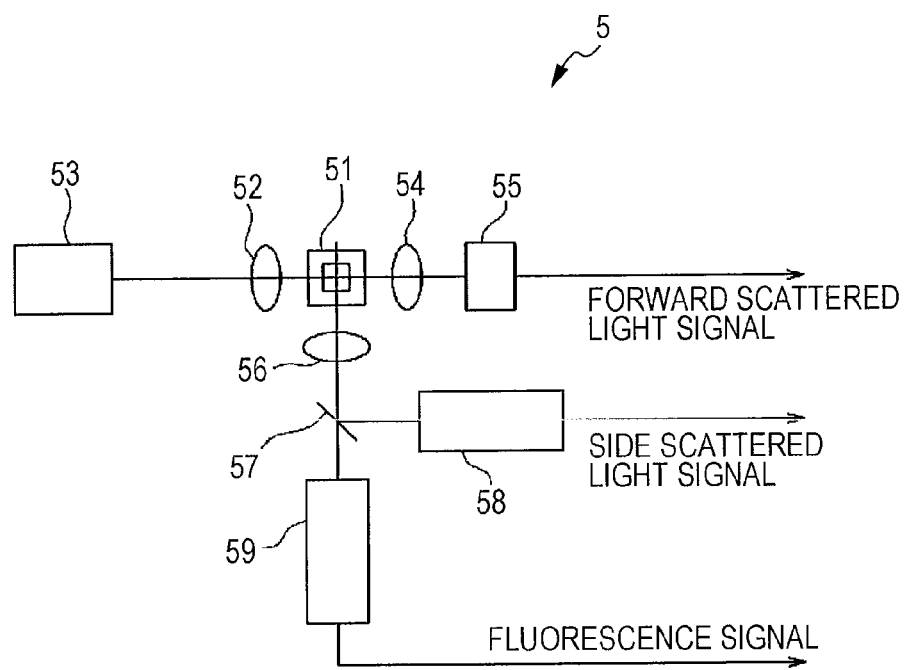
FIG. 3 illustrates a configuration of the FCM section.

FIG. 3 is a view illustrating a configuration of the FCM section 5. A condenser lens 52 condenses the laser light radiated from a laser light source 53 onto the sheath flow cell 51. A light collecting lens 54 collects the forward scattered light emitted from the cells or particles in the measurement specimen running in the sheath flow cell 51 and directs the collected light to a forward scattered light detector 55, hereinafter referred as FSC detector 55. A light collecting lens 56 collects the side scattered light and the fluorescence emitted from the cells or particles in the measurement specimen running in the sheath flow cell 51 and directs to a dichroic mirror 57. The dichroic mirror 57 reflects the side scattered light toward a side scattered light detector 58, hereinafter referred as SSC detector 58. The dichroic mirror 57 transmits the fluorescence toward a fluorescence light detector 59, hereinafter referred as FL detector 59. Each of the FSC detector 55, the SSC detector 58, and the FL detector 59 converts the received light to an electric signal in preset sensitivity, and outputs forward scattered light signal (FSC), the side scattered light signal (SSC) and the fluorescence signal (FL) according to an intensity of received light. The output signal is amplified by a pre-amplifier (not shown), and provided for the process in the next stage. Each of the FSC detector 55, the SSC detector 58, and the FL detector 59 can output signal in a low sensitivity and in a high sensitivity by switching drive voltages supplied to them. In the high sensitivity, the conversion of received light to electrical signal is made in high amplification factor lather than the low sensitivity. The switching of the sensitivity is carried out by the microcomputer 11 as described later. A photodiode, a photo-multiplier tube, and the like can be used for the FSC detector 55. Similarly, a photodiode, a photo-multiplier tube, and the like can be used for the SSC detector 58 and the FL detector 59. The fluorescence signal (FL) output from the FL detector 59 is, after being amplified by a preamplifier (not shown), applied to branched two signal channels. The two signal channels are connected to the amplifier circuit 50, respectively. The fluorescence signal (FL) input to one signal channel is amplified with high sensitivity by the amplifier circuit 50. This signal channel is referred as "High-CH". Fluorescence signal (FL) amplified by the High-CH is referred as first fluorescence signal (FLH). The fluorescence signal (FL) input to another signal channel is amplified with low sensitivity by the amplifier circuit 50. This signal channel is referred as "Low-CH". Fluorescence signal (FL) amplified by the Low-CH is referred as second fluorescence signal (FLL).

Figure 4:
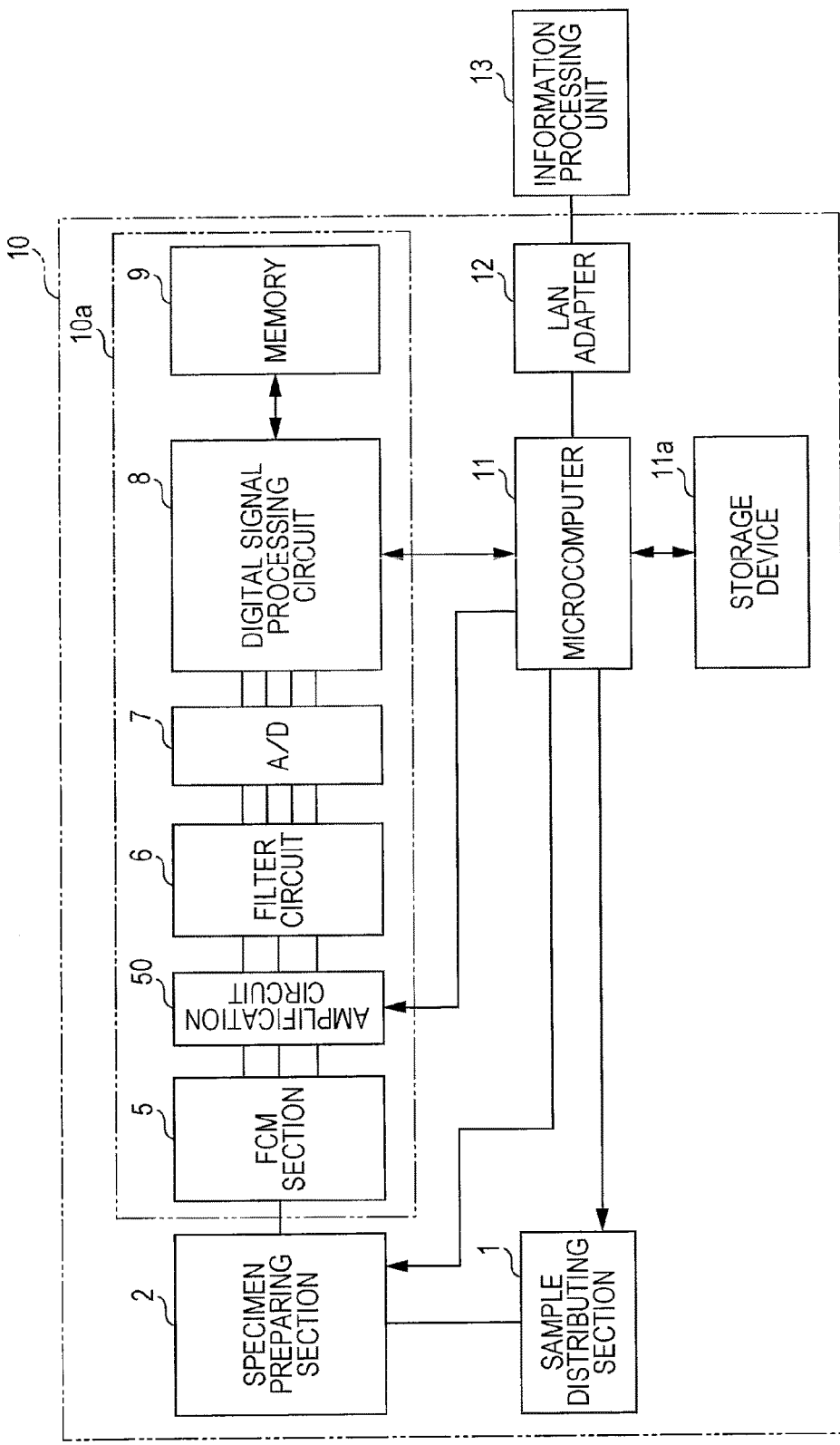
FIG. 4 is a block diagram illustrating a configuration of the urine sample analyzer according to the embodiment.

FIG. 4 is a block diagram illustrating a configuration of the urine sample analyzer 100. The measurement unit 10 includes the sample distributing section 1, the specimen preparing section 2, and the FCM section 5 described above, an amplifier circuit 50 for amplifying the output signal that has been amplified by the pre-amplifier of the FCM section 5, a filter circuit 6 for filtering the output signal from the amplifier circuit 50, an A/D converter 7 for converting the analog output signal of the filter circuit 6 to a digital signal, a digital signal processing circuit 8 for processing the digital signal, a memory 9 connected to the digital signal processing circuit 8, the microcomputer 11 and an LAN adapter 12 connected to the microcomputer 11. The microcomputer 11 is connected to the specimen preparing section 2, the amplifier circuit 50, and the digital signal processing circuit 8. The information processing unit 13 is connected to the measurement unit 10 with the LAN cable through the LAN adapter 12, where the measurement data acquired by the measurement unit 10 is transmitted to the information processing unit 13 for analysis thereby. The FCM section 5, the amplifier circuit 50, the filter circuit 6, the A/D converter 7, the digital signal processing circuit 8, and the memory 9 configure a detecting section 10a. The detecting section 10a derives signals from cells in the measurement specimens and generates measurement data for analysis by the information processing unit 13.

The syringe pump 20b of the specimen preparing section 2 can adjust the push-out amount per unit time of the measurement specimen. The flow rate per unit time of the measurement specimen supplied to the sheath flow cell 51 from the syringe pump 20b can be adjusted by adjusting the push-out amount per unit time of the measurement specimen. The control of syringe pump 20b is carried out by the microcomputer 11.

Gain of the amplifier circuit 50 can be adjusted in several levels. The microcomputer 11 can adjust the sensitivity of the amplifier circuit 50 by setting the gain of the amplifier circuit 50.

A storage device 11a is connected to the microcomputer 11. Such storage device is configured by a flash memory or other computer-readable media. The control program of the measurement unit 10 executed by the microcomputer 11, and the data used by the relevant control program are stored in the storage device 11a. The microcomputer 11 can operate the measurement unit 10, as will be described later, by executing the control program stored in the storage device 11a.

Referring back to FIG. 2, the first through fourth reagents are mentioned. The first reagent 19u is a buffer solution containing a buffering agent as its main component. The first reagent 19u contains osmotic pressure compensating agent to make cells suitably be stained by the third reagent 18u without lysing red blood cells. The osmotic pressure of the first reagent 19u is adjusted not to lyse red blood cells in urine, particularly in the range of 100 to 600 mOsm/kg so that classification measurements of urinary sediments are suitably performed. The first reagent 19u is free from a hemolytic agent having a hemolytic effect on red blood cells in urine.

The second reagent 19b has hemolytic effect, as opposed to the first reagent 19u. This is to enhance the stain of the fourth reagent 18b to the cell membrane of the bacteria to rapidly advance the dyeing. This is also to contract foreign substances such as threads, erythrocyte pieces, and the like. The second reagent 19b contains a surfactant as a hemolytic agent to earn a hemolytic effect to red blood cells in urine. The surfactant may be selected from anionic surfactant, nonionic surfactant, and cationic surfactant. The cationic surfactant is particularly suitable. The nucleic acid of bacteria can be more efficiently stained by the dye contained in the fourth reagent 18b since the cell membrane of the bacteria can be damaged by the surfactant. As a result, staining of the bacteria can be made in a short time.

The second reagent 19b may obtain the hemolytic effect by being acidic or adjusted to low pH, instead of containing a surfactant. In the embodiment, low pH means that the pH of the second reagent 19b is lower than the pH of the first reagent 19u. In the embodiment, the first reagent 19u is within a range of neutral or mild acidity to mild alkaline, and the second reagent 19b is acidic or strongly acidic. The pH of the first reagent 19u is between 6.0 and 8.0. The pH of the second reagent 19b is lower than 6.0 and is preferably between 2.0 and 6.0.

The second reagent 19b may contain the surfactant and be adjusted to low pH.

In another embodiment, the second reagent 19b may acquire the hemolytic effect by lowering the osmotic pressure than the first reagent 19u.

In contrast to the second reagent 19b, the first reagent 19u does not contain a surfactant. The first reagent 19u may contain a surface, but it is necessary to adjust the type and concentration so as not to lyse erythrocytes. Thus, even if the first reagent 19u contains a surfactant, it should be lower concentration than that of the second reagent 19b, or it should be selected from the groups having weaker hemolytic effect than the second reagent 19b.

The third reagent 18u contains a dye used for the measurement of the urine sediments, including red blood cells, white blood cells, epidermal cells, casts, and so on. As the dye of the third reagent 18u, a dye having a staining effect on membrane of cell which does not contain nucleic acids is preferably selected. The third reagent 18u preferably contains an osmotic pressure compensating agent for the purpose of preventing red blood cells hemolysis and for the purpose of obtaining stable fluorescence intensity. The osmotic pressure of the third reagent 18u is adjusted in a range of 100 to 600 mOsm/kg so that the osmotic pressure of measurement specimen is suited for classification measurement. The cell membrane and the nucleus of the urine sediment are stained by the third reagent 18u. The condensed benzene derivatives are preferably used for the dye of the third reagent 18u. For example, cyanine dye can be used. The third reagent 18u may stain not only the cell membrane but also the nucleus membrane. With use of such third reagent 18u, nucleated cells such as white blood cells, epithelium, and the like, are stained stronger than anucleate cells. Therefore, the nucleated cells such as white blood cells and epithelium can be discriminated from the anucleate cells such as red blood cells by difference of degree of stain. As the third reagent 18u, reagent disclosed in U.S. Pat. No. 5,891,733 can be employed. U.S. Pat. No. 5,891,733 is herein incorporated by reference. The third reagent 18u is mixed with urine or body fluid with the first reagent 19u.

The fourth reagent 18b contains a dye that enables accurate measurement of bacteria even if a sample to be measured contains foreign substances having a similar size with bacteria. The detailed description of the fourth reagent 18b can be found in EP 1136563A. As the dye of the fourth reagent 18b, dye staining nucleic acid is preferably selected. The cyanine dye of U.S. Pat. No. 7,309,581 can be used for the dye. EP 1136563 A and U.S. Pat. No. 7,309,581 are herein incorporated by reference. The fourth reagent 18b is mixed with urine or body fluid with the second reagent 19b.

Therefore, the third reagent 18u preferably contains a dye for staining cell membrane, and the fourth reagent 18b preferably contains a dye for staining nucleic acid. Even if a urine sample contains anucleate cells such as red blood cells, the third reagent 18u makes it possible to stain and detect the anucleate cells. Furthermore, even if a urine sample contains bacteria, the fourth reagent 18b makes it possible to stain the nucleic acid of the bacteria and detect them.

For the first reagent 19u, UFII pack-SED (manufactured by Sysmex Co.) can be used. The first reagent 19u is contained in the reagent container, and the first reagent 19u can be supplied to the reaction chamber 2u by setting the reagent container in the analyzer. For the third reagent 18u, UFII search-SED (manufactured by Sysmex Co.) can be used. The third reagent 18u is contained in the reagent container, and the third reagent 18u can be supplied to the reaction chamber 2u by setting the reagent container in the analyzer. The first reagent 19u and the third reagent 18u are also used for the measurement of red blood cells in the body fluid, in the body fluid measurement mode.

For the second reagent 19b, UFII pack-BAC (manufactured by Sysmex Co.) can be used. The second reagent 19b is contained in the reagent container, and the second reagent 19b can be supplied to the reaction chamber 2u by setting the reagent container in the analyzer. For the fourth reagent 18b, UFII search-BAC (manufactured by Sysmex Co.) can be used. The fourth reagent 18b is contained in the reagent container, and the fourth reagent 18b can be supplied to the reaction chamber 2u by setting the reagent container in the analyzer. The second reagent 19b and the fourth reagent 18b are also used for the measurement of white blood cells, large cells, and bacteria in the body fluid, in the body fluid measurement mode. The UFII pack-BAC has a hemolytic effect by being adjusted to a low pH than the UFII pack-SED.

In the body fluid measurement mode, the second reagent 19b having a hemolytic effect is used to measure white blood cells, large cells, and bacteria. In general, the concentration of red blood cells in urine is a few hundred per 1 μL at most. Urine that contains red blood cells number of more than one thousand per 1 μL is rare. On the other hand, body fluid sometimes contains red blood cells in concentration of ten thousand per 1 μL. If a body fluid contains a great amount of red blood cells, they may inhibit the accurate measurement of white blood cells and large cells in the body fluid. In the embodiment, since red blood cells in body fluid are hemolyzed by the second reagent 19b having the hemolytic effect, white blood cells and large cells in body fluid can be measured at high accuracy without being inhibited by red blood cells. Furthermore, in the cells such as white blood cells, large cells, and bacteria, the cell membrane are damaged by the second reagent 19b having the hemolytic effect. The transmissivity of the dye is enhanced.

The measurement of the U-BAC prepared using the second reagent 19b is preferably carried out after the U-SED since the second reagent 19b has a hemolytic effect. Such measurement order is particularly preferable if the second reagent 19b contains a surfactant. If the measurement of the U-SED is carried out after U-BAC, the surfactant of the U-BAC may remain in the flow path and mix with the U-SED in case carry-over occurs. It may cause a damage of membrane of red blood cells, and affect the measurement of the urine sediment. According to such configuration, the surfactant can be prevented from mixing with the U-SED.

The third reagent 18u and the fourth reagent 18b preferably have the peak of the absorption wavelength existing in the vicinity of the light emission wavelength of the laser light source 53. The stained urine sediment and bacteria can be optically measured by selecting the peaks of the absorption wavelength of the third reagent 18u and the fourth reagent 18b so as to exist in the vicinity of the light emission wavelength of the laser light source 53.

In the present embodiment, U-SED serving as the first measurement specimen for measuring urine sediments and U-BAC serving as the second measurement specimen for measuring bacteria are respectively prepared from one urine sample in the urine measurement mode. The urine sediments such as red blood cells and white blood cells are measured by the U-SED. The bacteria are measured by the U-BAC. Thus, the urine sediments and the bacteria can be respectively measured with one analyzer. The bacteria existing in great amounts in the urine can be measured at high accuracy by preparing the measurement specimen U-BAC for measuring the bacteria separately from the measurement specimen U-SED for measuring the red blood cells, the white blood cells, and the like. In the body fluid measurement mode, BF-RBC serving as the third measurement specimen for measuring red blood cells in the body fluid, and BF-WBC serving as the fourth measurement specimen for measuring white blood cells, large cells and bacteria in body fluid are respectively prepared from one body fluid sample. The red blood cells in the body fluid are measured by the BF-RBC. The white blood cells, large cells, and bacteria in the body fluid are measured by the BF-WBC. Even with the body fluid containing red blood cells in greater amount than urine, the white blood cells can be accurately measured without being subjected to the influence of red blood cells by preparing the BF-WBC with the second reagent 19b having a hemolytic effect. Furthermore, since the concentration of bacteria in the body fluid is lower than that of urine, a constant measurement accuracy can be ensured even if the bacteria, white blood cells, and large cells are measured together using the same measurement specimen in the case of the body fluid. Thus, the red blood cells, white blood cells, large cells, and bacteria in the body fluid can be measured efficiently at high accuracy with one analyzer.

In the embodiment, the first reagent 19u and the third reagent 18u are commonly used in the measurement of the urine sediment in the urine measurement mode and the measurement of red blood cells in the body fluid in the body fluid measurement mode. The second reagent 19b and the fourth reagent 18u are commonly used in the measurement of bacteria in the urine measurement mode and the measurement of white blood cells, large cells, and bacteria in the body fluid in the body fluid measurement mode. Furthermore, the common reaction chamber 2u is used in the measurement of the urine sediment in the urine measurement mode and the measurement of red blood cells in the body fluid in the body fluid measurement mode. The common reaction chamber 2b is used in the measurement of bacteria in the urine measurement mode and the measurement of white blood cells, large cells, and bacteria in the body fluid in the body fluid measurement mode. Thus, complication that arises when separately arranging the device configuration dedicated for urine measurement and the device configuration dedicated for body fluid measurement can be prevented by making the reagents and the reaction chamber common in the urine measurement mode and the body fluid measurement mode.

Moreover, FCM section 5 is commonly used in measurements of urine sediment, urine bacteria, red blood cells in body fluid, and nucleated cells and bacteria in body fluid. It makes possible to simplify the configuration of analyzer, reduce manufacturing cost, and downsize the device.

Figure 5:
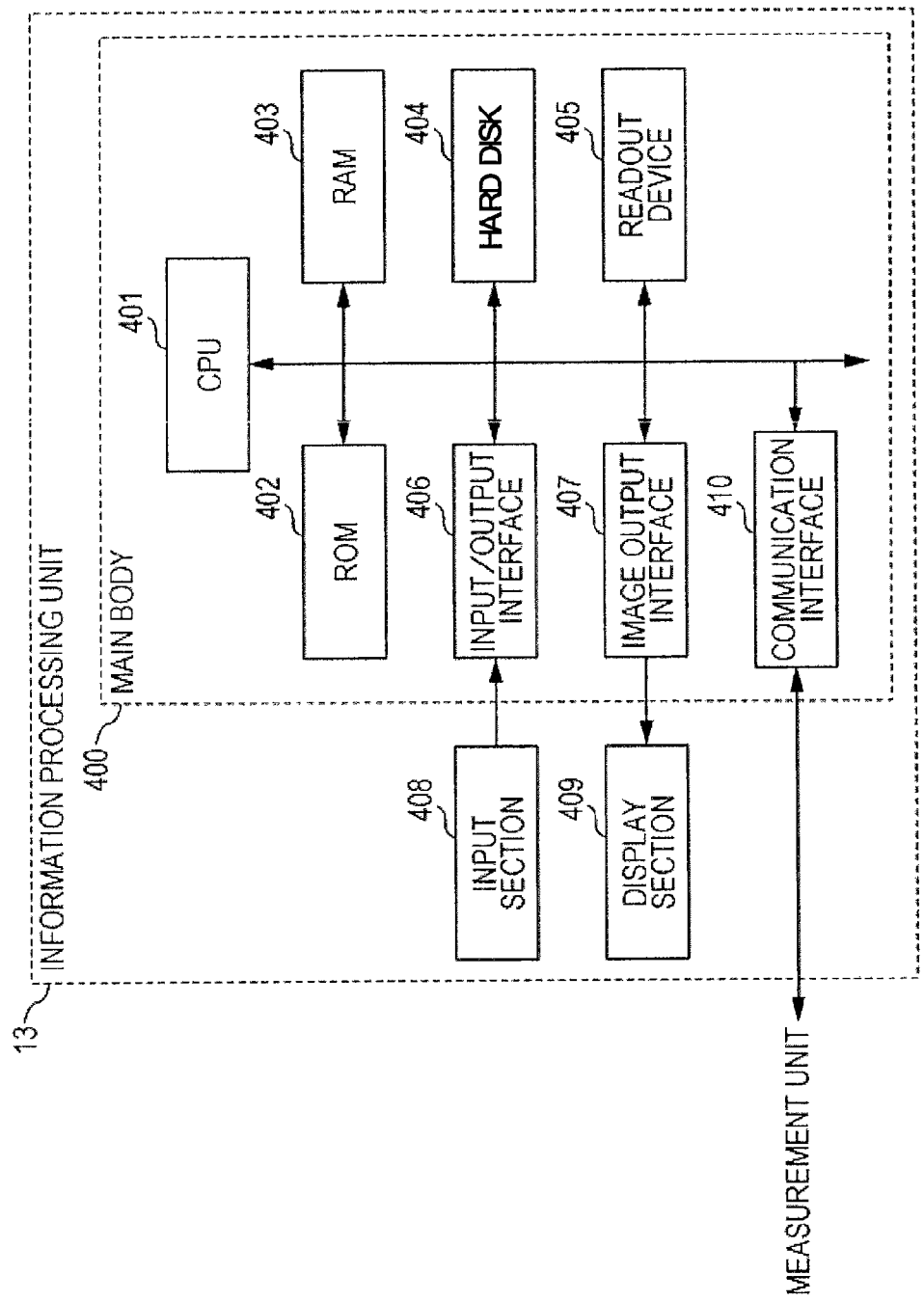
FIG. 5 is a block diagram illustrating a configuration of an information processing unit.

FIG. 5 is a block diagram illustrating a configuration of the information processing unit 13. The information processing unit 13 includes a personal computer, and includes a main body 400, an input section 408, and a display section 409. The main body 400 includes a CPU 401, a ROM 402, a RAM 403, a hard disk 404, a readout device 405, an input/output interface 406, an image output interface 407, and a communication interface 410.

The CPU 401 executes computer programs stored in the ROM 402 and the computer programs loaded in the RAM 403. The RAM 403 is used to read out the computer programs recorded on the ROM 402 and the hard disk 404. In executing the computer programs, the RAM 403 is also used as a work region of the CPU 401.

The hard disk 404 is installed with various computer programs to be executed by the CPU 401 such as operating system and application program, as well as data used in executing the computer program. In other words, the hard disk 404 is installed with the computer program for analyzing the measurement data provided from the measurement unit 10, and outputting the analysis result.

The readout device 405 is configured by a CD drive, DVD drive, and the like, and can read out the computer programs and data recorded on a recording medium. The input section 408 including a mouse and a keyboard is connected to the input/output interface 406, and where the user uses the input section 408 to input data to the information processing unit 13. The image output interface 407 is connected to the display section 409 configured by a liquid crystal panel, and the like, and outputs the video signal corresponding to the image data to the display section 409. The display section 409 displays the image based on the input video signal. The information processing unit 13 is connected to the measurement unit 10 by way of the communication interface 410, and can transmit and receive data with respect to the measurement unit 10 by the communication interface 410.

<Operation of Urine Sample Analyzer>

The operation of the urine sample analyzer according to the present embodiment will be hereinafter described.

(Setting of Measurement Mode)

Figure 6:
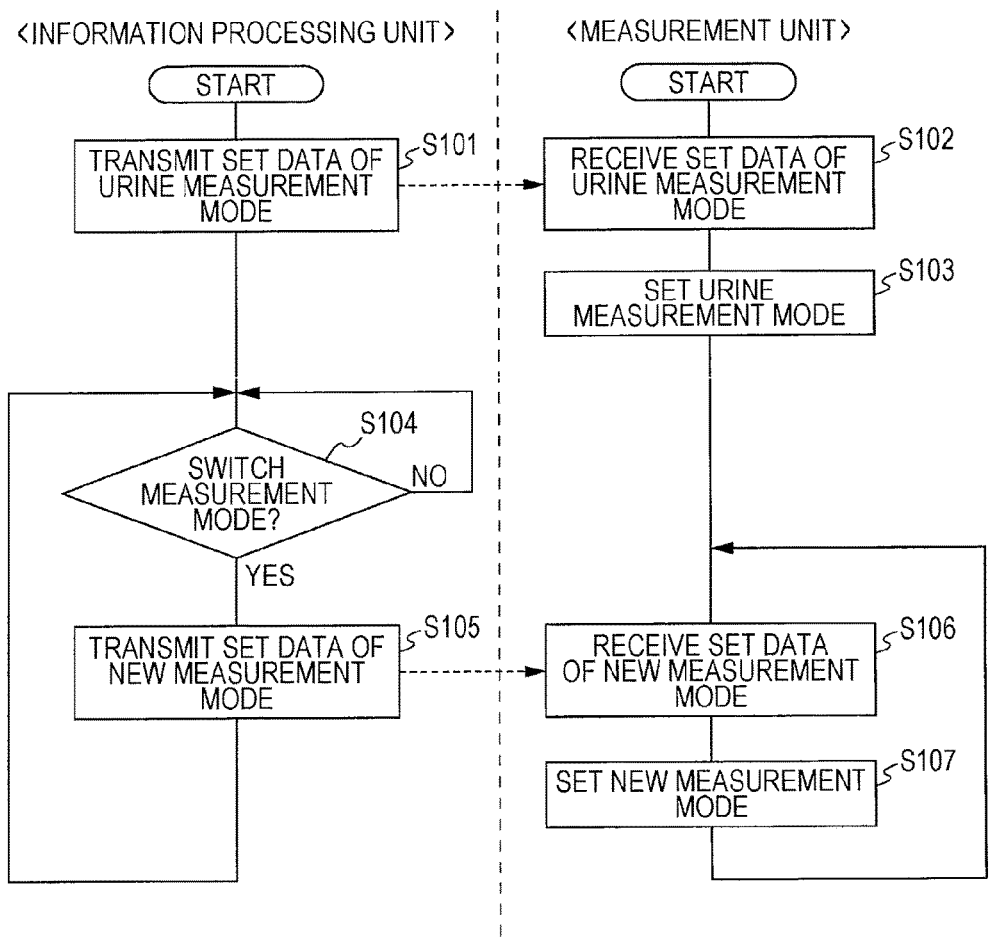
FIG. 6 is a flowchart illustrating a procedure of a measurement mode setting process in the urine sample analyzer according to the embodiment.

FIG. 6 is a flowchart illustrating a procedure of a measurement mode setting process in the urine sample analyzer according to the present embodiment. When the urine sample analyzer 100 is turned ON, the initialization process is executed in the microcomputer 11 and the CPU 401. In the initialization process of the CPU 401, the setting data for setting the measurement mode to the urine measurement mode is transmitted to the measurement unit 10 (step S101). When the measurement unit 10 receives the setting data (step S102), the microcomputer 11 stores the set value for the urine measurement mode in the embedded memory of the microcomputer 11. The urine measurement mode is thereby set (step S103). Therefore, the measurement mode of the sample analyzer 100 is set to urine measurement mode as default.

The urine sample analyzer 100 is thus set to the urine measurement mode in the initial state. The set value for the urine measurement mode includes sensitivity set values of the FSC detector 55, the SSC detector 58 and the FL detector 59, the gain set value of the amplification circuit 50, the set value of the push-out amount per unit time of the syringe pump 20b and the set value of the measurement time in the urine sediment measurement. The set value also includes the sensitivity set values of the FSC detector 55, the SSC detector 58 and the FL detector 59, the gain set value of the amplification circuit 50, the set value of the push-out amount per unit time of the syringe pump 20b and the set value of the measurement time in the bacteria measurement.

Figure 7:
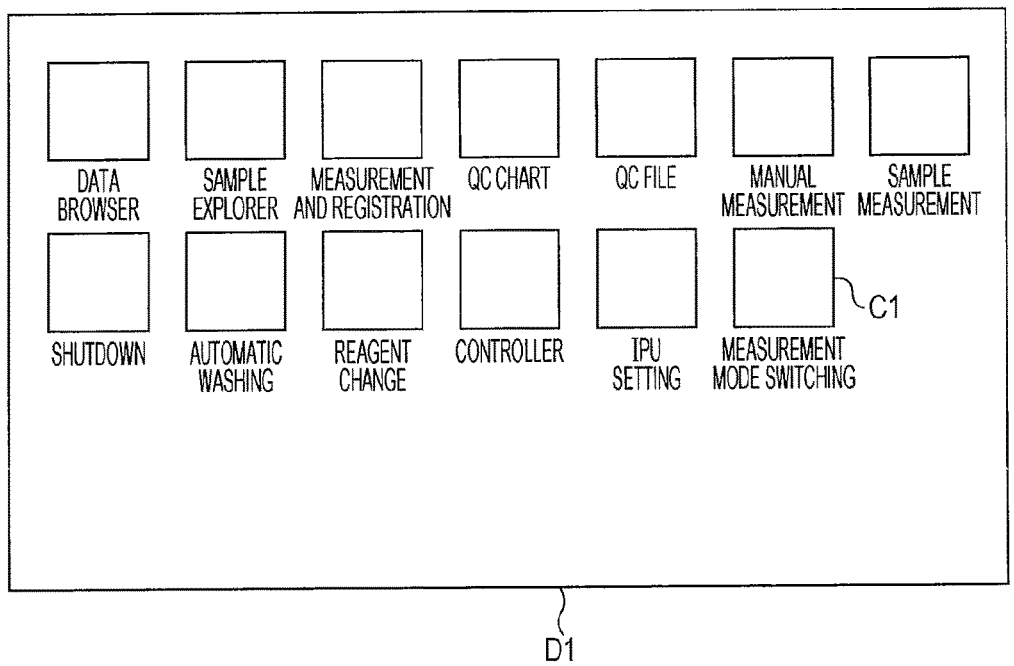
FIG. 7 illustrates an example of a display screen of the information processing unit.

The user can operates the input section 408 of the information processing unit 13 to switch the measurement mode. FIG. 7 is a view illustrating an example of a display screen of the information processing unit 13. A menu screen D1 is displayed on the display section 409. In the menu screen D1, a plurality of icons are lined. The icons are selectable by the operation of the input section 408. The menu screen D1 includes an icon C1 for switching the measurement mode.

Figure 8:
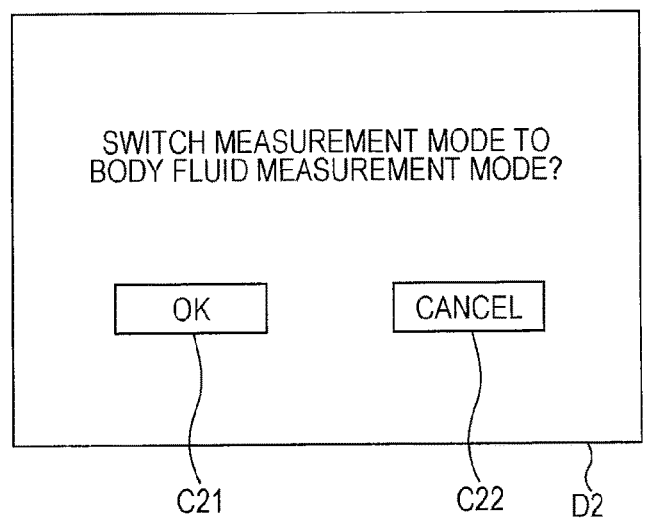
FIG. 8 illustrates a measurement mode switching confirmation dialogue.

When the icon C1 is selected by the user, a dialogue D2 for measurement mode switching confirmation is displayed on the display section 409. FIG. 8 is a view illustrating the dialogue. The dialogue D2 includes a message asking to confirm whether to switch the measurement mode, an OK button C21, and a cancel button C22. The OK button C21 and the cancel button C22 are respectively selectable by the operation of the input section 408. The user selects the OK button C21 when executing the switching of the measurement mode, and selects the cancel button C22 when cancelling the switching of the measurement mode. When the OK button C21 is selected, an instruction to switch the measurement mode is given to the CPU 401 and then the dialogue D2 is closed. When the cancel button C22 is selected, on the other hand, the dialogue D2 is closed without giving an instruction to switch the measurement mode to the CPU 401.

The CPU 401 determines whether or not the instruction to switch the measurement mode is given (step S104). If the instruction is not given (NO in step S104), the CPU 401 repeats the process of step S104 until the instruction is given. If the instruction to switch the measurement mode is given (YES in step S104) as described above, the setting data for switching the measurement mode is transmitted to the measurement unit 10 (step S105). That is, the setting data for setting the body fluid measurement mode is transmitted to the measurement unit 10 when the current measurement mode is the urine measurement mode. And the setting data for setting the urine measurement mode is transmitted to the measurement unit 10 when the current measurement mode is the body fluid measurement mode. After the process of step S105, the CPU 401 returns the process to step S104.

When the measurement unit 10 receives the setting data (step S106), the microcomputer 11 stores the mode set value for the new measurement mode in the embedded memory of the microcomputer 11. That is, the mode set value for the body fluid measurement mode is stored in the embedded memory when setting the body fluid measurement mode, and the set value for the urine measurement mode is stored in the embedded memory when setting the urine measurement mode. The new measurement mode is thereby set (step S107). After the process of step S107, the microcomputer 11 returns the process to step S106.

The set value for the body fluid measurement mode includes sensitivity set values of the FSC detector 55, the SSC detector 58 and the FL detector 59, the gain set value of the amplification circuit 50, the set value of the push-out amount per unit time of the syringe pump 20b and the set value of the measurement time in the red blood cell measurement in the body fluid. The set value also includes the sensitivity set values of the FSC detector 55, the SSC detector 58 and the FL detector 59, the gain set value of the amplification circuit 50, the set value of the push-out amount per unit time of the syringe pump 20b and the set value of the measurement time in the nucleated cell/bacteria measurement in the body fluid.

(Sample Measurement Operation in Urine Measurement Mode)

Figure 9:
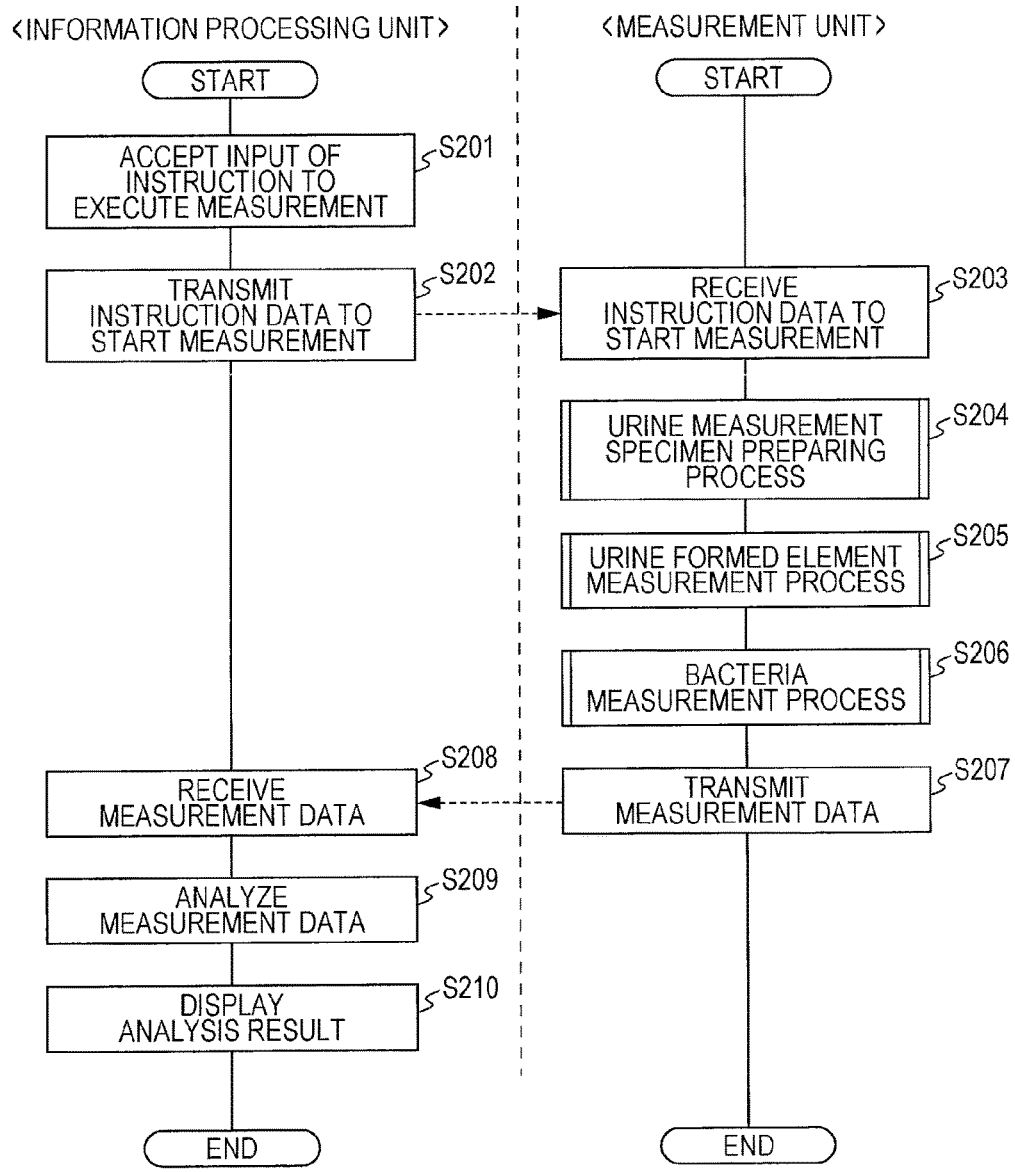
FIG. 9 is a flowchart illustrating a procedure of a sample measurement process of the urine sample analyzer in a urine measurement mode.

The sample measurement operation in the urine measurement mode of the urine sample analyzer 100 will now be described. FIG. 9 is a flowchart illustrating a procedure of a sample measurement process of the urine sample analyzer 100 in the urine measurement mode. First, an instruction to execute the measurement is input from the input section 408 of the information processing unit 13 (step S201). Upon receiving such instruction, the CPU 401 transmits the instruction data instructing the start of measurement to the measurement unit 10 (step S202). When the measurement unit 10 receives the instruction data (step S203), the microcomputer 11 executes a urine measurement specimen preparing process (step S204), a urine sediment measurement process (step S205), and a bacteria measurement process (step S206).

Figure 10:
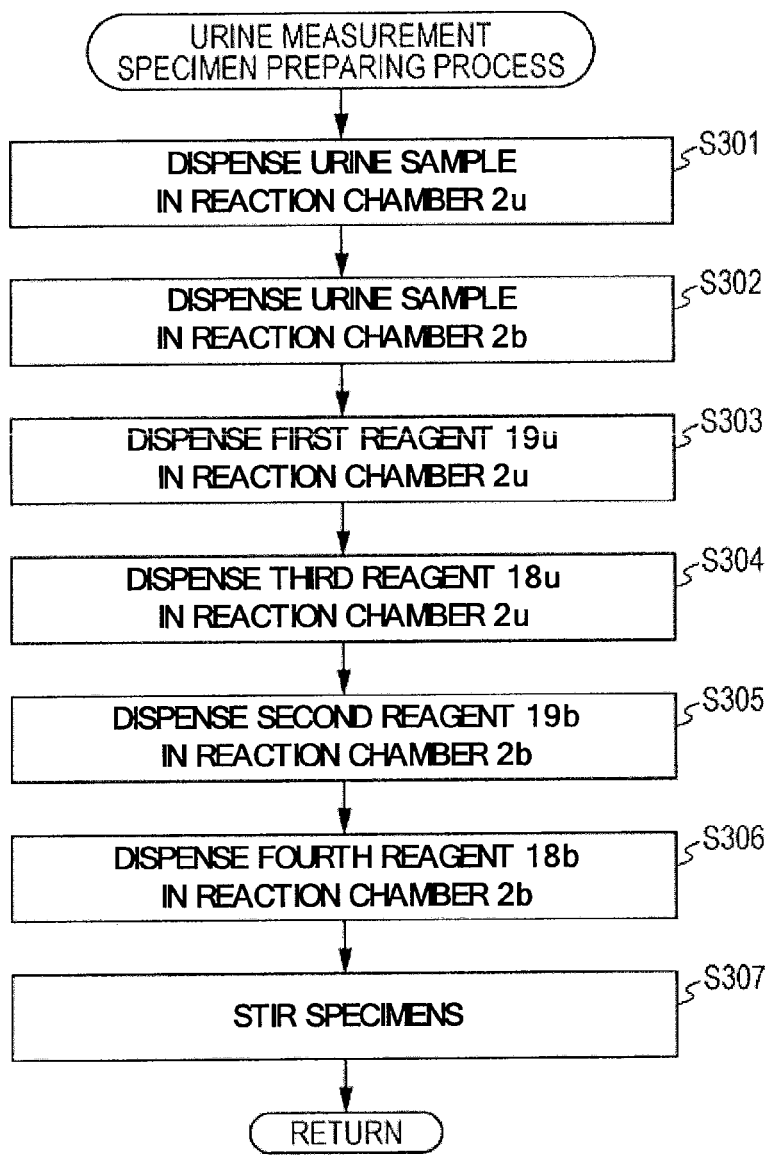
FIG. 10 is a flowchart illustrating a procedure of a urine measurement specimen preparing process.

FIG. 10 is a flowchart illustrating a procedure of the urine measurement specimen preparing process. In the urine measurement specimen preparing process, the microcomputer 11 first controls the sample distributing section 1 to cause the aspirating tube 17 to aspirate a predetermined amount of urine sample from the test tube T and dispense aliquots of the predetermined amount of urine sample to the reaction chamber 2u and the reaction chamber 2b (steps S301, S302).

A predetermined amount of first reagent 19u and third reagent 18u are quantified and dispensed to the reaction chamber 2u (step S303 and step S304). Similarly, a predetermined amount of second reagent 19b and fourth reagent 18b are quantified and dispensed to the reaction chamber 2b (step S305 and step S306). The reaction chamber 2u and the reaction chamber 2b are respectively warmed to a predetermined temperature by a heater (not shown). The mixture of dispensed sample and reagents is stirred with a stirring tool (not shown) such as a propeller (step S307). The U-SED is thereby prepared in the reaction chamber 2u, and the U-BAC is prepared in the reaction chamber 2b. After the process of step S307 is finished, the microcomputer 11 returns the process to the main routine.

The first reagent 19u dispensed to the reaction chamber 2u in step S303 does not have a hemolytic effect, and hence the cell membranes of red blood cells, white blood cells, and other cells are not damaged. The second reagent 19b dispensed to the reaction chamber 2b in step S305, on the other hand, has a hemolytic effect, and hence the cell membranes of bacteria is damaged and nucleic acid of the bacteria can be efficiently stained.

Figure 11:
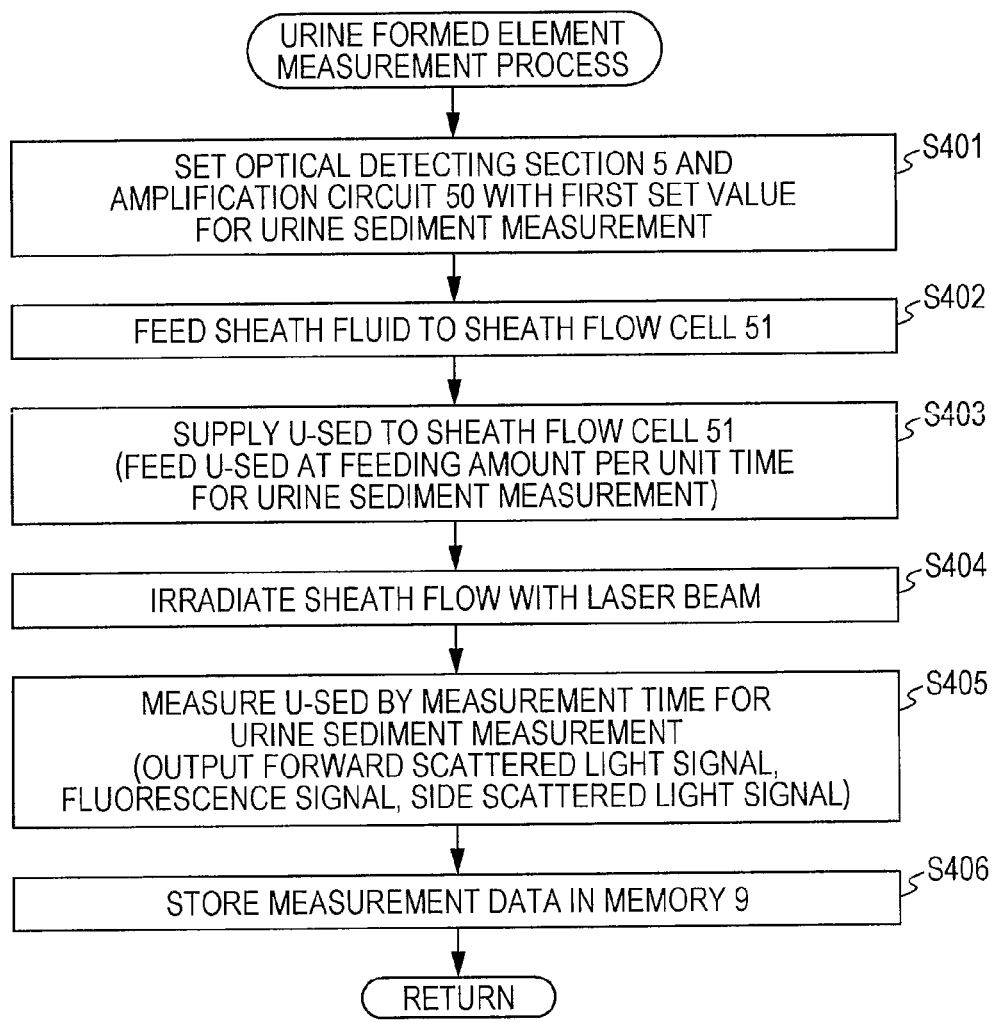
FIG. 11 is a flowchart illustrating a procedure of a urine sediment measurement process.

FIG. 11 is a flowchart illustrating a procedure of a urine sediment measurement process. In the urine sediment measurement process, the microcomputer 11 first sets the sensitivities of the FSC detector 55, the SSC detector 58, and the FL detector 59, and the gain of the amplification circuit 50 with the first set value for the urine sediment measurement (step S401). The microcomputer 11 then causes the compressor 22a to supply the compressed air to the sheath fluid accommodating portion 22 to feed the sheath fluid to the sheath flow cell 51 (step S402). The U-SED is supplied from the reaction chamber 2u to the sheath flow cell 51 while the supply of sheath fluid to the sheath flow cell 51 is continued (step S403).

The details of the process of step S403 will now be described. First, the electromagnetic valve 21a is opened, the electromagnetic valve 21b is closed, and the electromagnetic valves 21c, 21d are opened. The syringe pump 20a is driven in this state so that the U-SED in the reaction chamber 2u is aspirated by the syringe pump 20a. The U-SED is filled in the tube within a range between the electromagnetic valve 21c and the electromagnetic valve 21d. Then, the electromagnetic valves 21c, 21d are closed and the syringe pump 20b is driven, so that the U-SED filled between the electromagnetic valve 21c and the electromagnetic valve 21d is pushed out toward the sheath flow cell 51. In this case, the syringe pump 20b is driven according to the push-out amount per unit time which defined by the first set value for the urine sediment measurement.

As a result of the above, the sheath fluid and the U-SED are simultaneously supplied to the sheath flow cell 51, and a flow of the U-SED diluted and enveloped by the sheath fluid is formed in the sheath flow cell 51. The flow of U-SED is irradiated with the laser beam from the laser light source 53 (step S404). When a particle or a cell in the U-SED passes through the sheath flow cell 51, forward scattered light, fluorescence light, and side scattered light are generated. The forward scattered light, the fluorescence light, and the side scattered light are respectively received by the FSC detector 55, the FL detector 59, and the SSC detector 58 and converted to the electric signals (step S405). The measurement of U-SED in step S405 is carried out for a time defined by the first set value for the urine sediment measurement.

The electric signals corresponding to the light receiving levels of the FSC detector 55, the FL detector 59, and the SSC detector 58 are output as the forward scattered light signal (FSC), the first fluorescence signal (FLH), the second fluorescence signal (FLL) and the side scattered light signal (SSC). Such output signals are amplified by the amplification circuit 50. In this case, the signals are output from the FSC detector 55, the FL detector 59, and the SSC detector 58 at the sensitivity defined by the first set value for the urine sediment measurement set in step S401, and the output signals of the FSC detector 55, the FL detector 59, and the SSC detector 58 are amplified by the amplification circuit 50 at the amplification rate defined by the first set value. The sensitivity set values of the FSC detector 55, the SSC detector 58, and the FL detector 59 at the first set value are all low sensitivities. The forward scattered light signal (FSC), the first fluorescent signal (FLH), the second fluorescent signal (FLL) and the side scattered light signal (SSC) outputted from the amplifier circuit 50 in a state where the first set value is set are respectively referred as, FSC-1, FLH-1, FLL-1 and SSC-1. Hereafter, the signals output from the amplifier circuit 50 in a state in which nth first set value is set, referred to FSC-n, FLH-n, FLL-n, and SSC-n.

The amplified forward scattered light signal (FSC), the fluorescence signal (FL), and the side scattered light signal (SSC) are filtered by the filter circuit 6, converted to digital signals by the A/D converter 7, processed by the digital signal processing circuit 8, and stored in the memory 9 as measurement data (step S406). After the above processes are completed, the microcomputer 11 returns the process to the main routine.

Figure 12:
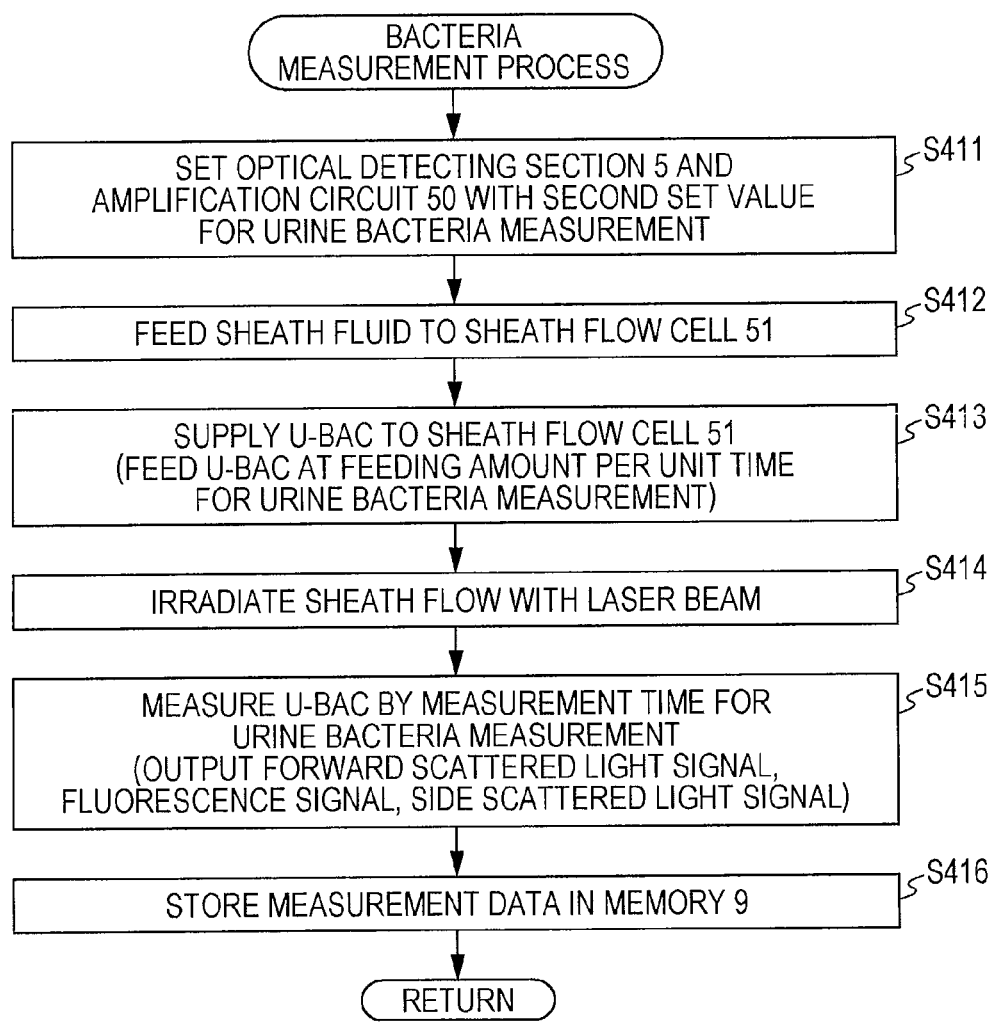
FIG. 12 is a flowchart illustrating a procedure of a measurement process of bacteria in the urine.

FIG. 12 is a flowchart illustrating a procedure of the bacteria measurement process. In the bacteria measurement process, the microcomputer 11 first sets the sensitivities of the FSC detector 55, the SSC detector 58, and the FL detector 59 and the gain of the amplification circuit 50 at the second set value for the bacteria measurement (step S411). The microcomputer 11 then causes the compressor 22a to supply the compressed air to the sheath fluid accommodating portion 22 to feed the sheath fluid to the sheath flow cell 51 (step S412). The U-BAC is supplied from the reaction chamber 2b to the sheath flow cell 51 while the supply of sheath fluid to the sheath flow cell 51 is continued (step S413).

The details of the process of step S413 will now be described. First, the electromagnetic valve 21a is closed, the electromagnetic valve 21b is opened, and the electromagnetic valves 21c, 21d are opened. The syringe pump 20a is driven in this state so that the U-BAC in the reaction chamber 2b is aspirated by the syringe pump 20a. The U-BAC is thereby filled in the tube within a range between the electromagnetic valve 21c and the electromagnetic valve 21d. Then, the electromagnetic valves 21c, 21d are closed and the syringe pump 20b is driven, so that the U-BAC filled between the electromagnetic valve 21c and the electromagnetic valve 21d is pushed out toward the sheath flow cell 51. In this case, the syringe pump 20b is driven at the push-out amount per unit time defined by the second set value for the bacteria measurement.

As a result of the above, the sheath fluid and the U-BAC are simultaneously supplied to the sheath flow cell 51, and a flow of the U-BAC diluted and enveloped by the sheath fluid is formed in the sheath flow cell 51. The flow of U-BAC is irradiated with the laser beam from the laser light source 53 (step S414). When a bacterium in the U-BAC passes through the sheath flow cell 51, forward scattered light, fluorescence light, and side scattered light are generated. The forward scattered light, the fluorescence light, and the side scattered light are respectively received by the FSC detector 55, the FL detector 59, and the SSC detector 58 and converted to the electric signal (step S415). The measurement of U-BAC in step S415 is carried out for a time defined by the second set value, determined in advance for the bacteria measurement.

The electric signals corresponding to the light receiving level of the FSC detector 55, the FL detector 59, and the SSC detector 58 are output as the forward scattered light signal (FSC), the first fluorescence signal (FLH), the second fluorescence signal (FLL) and the side scattered light signal (SSC). Such output signals are amplified by the amplification circuit 50. In this case, the signals are output from the FSC detector 55, the FL detector 59, and the SSC detector 58 at the sensitivity defined by the second set value for the bacteria measurement set in step S411, and the output signals of the FSC detector 55, the FL detector 59, and the SSC detector 58 are amplified by the amplification circuit 50 at the amplification rate defined by the second set value. The sensitivity set values of the FSC detector 55, the SSC detector 58, and the FL detector 59 at the second set value are all high sensitivities than the sensitivity set value defined by the first set value.

The amplified forward scattered light signal (FSC), the first fluorescence signal (FLH), the second fluorescence signal (FLL), and the side scattered light signal (SSC) are filtered by the filter circuit 6, converted to digital signals by the A/D converter 7, processed by the digital signal processing circuit 8, and stored in the memory 9 as measurement data (step S416). After the above processes are completed, the microcomputer 11 returns the process to the main routine.

After the bacteria measurement process described above, the microcomputer 11 transmits the measurement data generated by the urine sediment measurement process and the bacteria measurement process to the information processing unit 13 (step S207), and terminates the process.

When the information processing unit 13 receives the measurement data (step S208), the CPU 401 executes an analyzing process of the measurement data (step S209), generates an analysis result of the urine sample, and stores the analysis result in the hard disk 404.

In the analyzing process of step S209, red blood cells (RBC), white blood cells (WBC), epidermal cells (EC), and casts (CAST) are classified from the measurement data of the U-SED, and the respective cells are counted. Specifically, red blood cells (RBC) are classified from other particles and counted based on the intensity of the forward scattered light (FSC-1) and the intensity of the first fluorescence signal (FLH-1). White blood cells (WBC) are classified from other particles and counted based on the intensity of the forward scattered light signal (FSC-1) and the intensity of the second fluorescence signal (FLL-1). Epidermal cells (EC) and the casts (CAST) are classified and counted based on the first pulse width (FLLW) and the second pulse width (FLLW2) of the second fluorescence signal (FLL-1). Furthermore, drawing data for drawing a first distribution diagram (scattergram) in which cells of the U-SED are plotted at coordinates according to the intensity of the forward scattered light signal (FSC-1) and the intensity of the first fluorescence signal (FLH-1) is generated. Similarly, drawing data for drawing a second distribution diagram (scattergram) in which cells of the U-SED are plotted at coordinates according to the intensity of the forward scattered light signal (FSC-1) and the intensity of the second fluorescence signal (FLL-1) is generated. Furthermore, drawing data for drawing a third distribution diagram (scattergram) in which cells of the U-SED are plotted at coordinates according to the first pulse width (FLLW) and the second pulse width (FLLW2) of the second fluorescence signal (FLL-1) is similarly generated. The first pulse width (FLLW) and the second pulse width (FLLW2) of the second fluorescence signal (FLL-1) are respectively extracted by threshold values of different fluorescence intensities.

In the analyzing process of step S209, bacteria (BACT) of the U-BAC are detected and counted from the measurement data of the U-BAC. Specifically, the bacteria (BACT) are classified from other particles and counted based on the intensity of the forward scattered light signal (FSC-2) and the intensity of the first fluorescence signal (FLH-2). The drawing data for drawing a fourth distribution diagram (scattergram) in which the bacteria are plotted at coordinates according to the intensity of the forward scattered light signal (FSC) and the intensity of the first fluorescence signal (FLH-1) is also generated.

The CPU 401 then displays the analysis result obtained in the above manner on the display unit 409 (step S210), and terminates the process.

Figure 13:
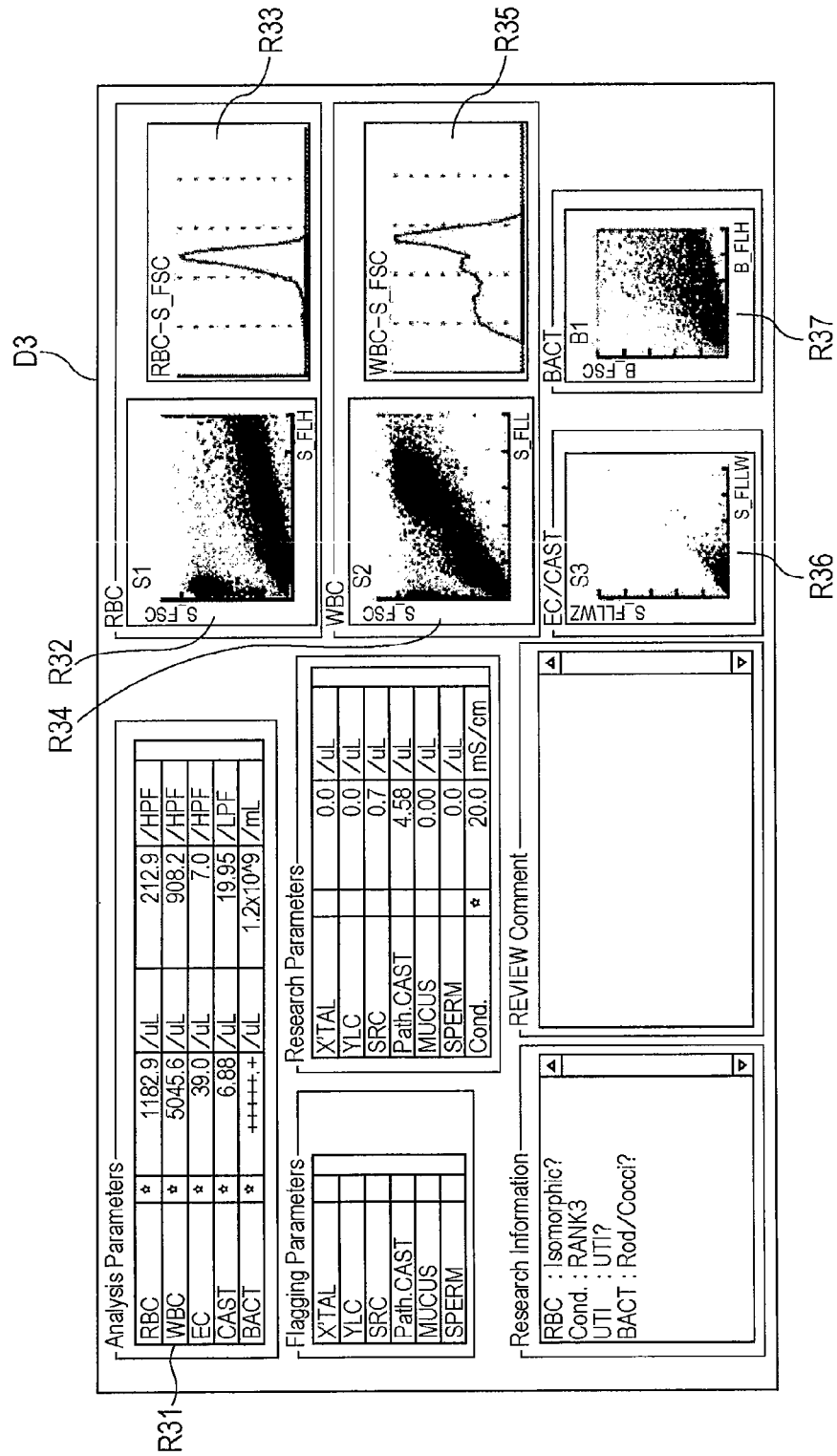
FIG. 13 illustrates an analysis result screen of the urine sample.

FIG. 13 is a view illustrating an analysis result screen of the urine sample. A urine sample analysis result screen D3 includes an analysis parameter section R31 showing counts of red blood cells, white blood cells, epidermal cells, casts, and bacteria. The screen also includes the first distribution diagram R32, a histogram R33 showing a particle size distribution of red blood cells with respects to the forward scattered light intensity, the second distribution diagram R34, a histogram R35 showing a particle size distribution of white blood cells with respects to the forward scattered light intensity, the third distribution diagram R36, and the fourth distribution diagram R37.

(Sample Measurement Operation in Body Fluid Measurement Mode)

Figure 14:
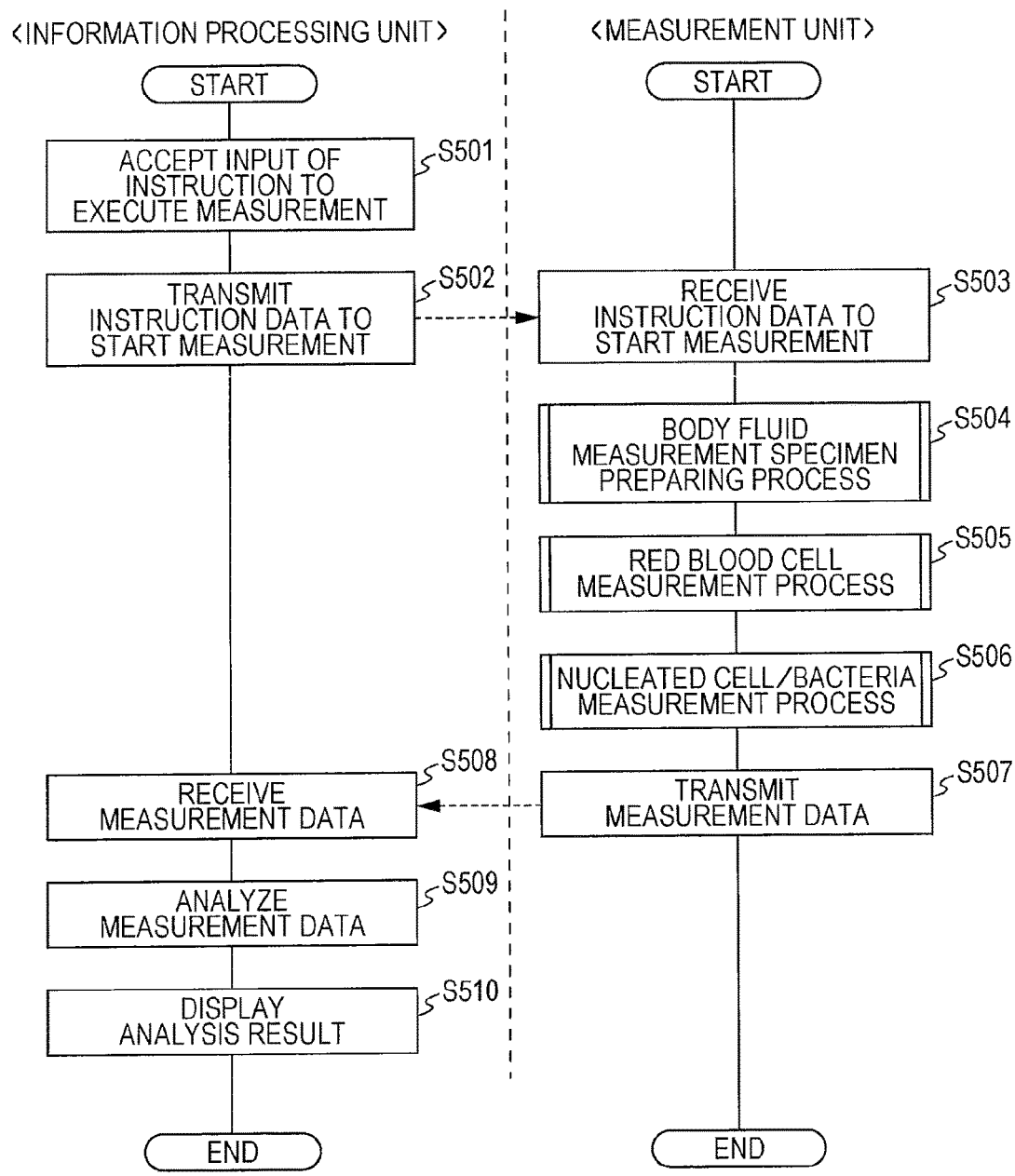
FIG. 14 is a flowchart illustrating a procedure of the sample measurement process of the urine sample analyzer in a body fluid measurement mode.

The sample measurement operation in the body fluid measurement mode of the urine sample analyzer 100 will now be described. FIG. 14 is a flowchart illustrating a procedure of the sample measurement process of the urine sample analyzer 100 in a body fluid measurement mode. First, an instruction to execute the measurement is input from the input section 408 of the information processing unit 13 (step S501). Upon receiving such instruction, the CPU 401 transmits the instruction data instructing the start of measurement to the measurement unit 10 (step S502). When the measurement unit 10 receives the instruction data (step S503), the microcomputer 11 executes a body fluid measurement specimen preparing process (step S504), a red blood cell measurement process (step S505), and a nucleated cell/bacteria measurement process (step S506).

Figure 15:
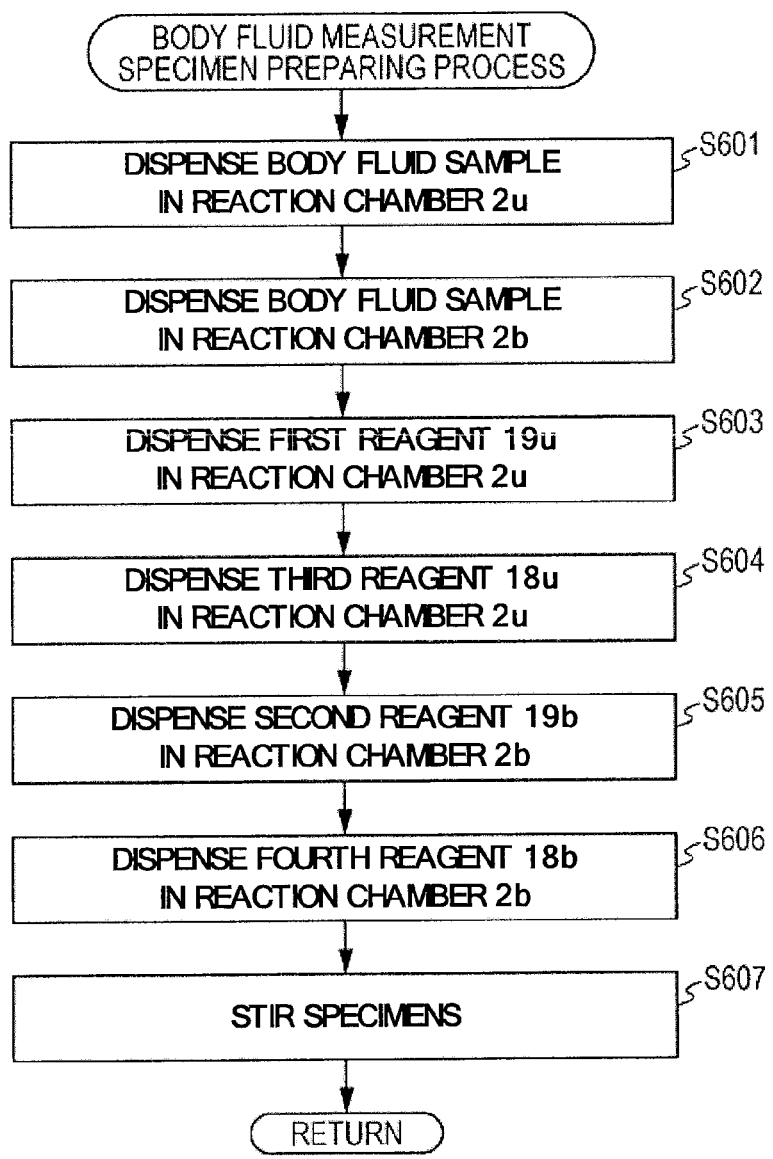
FIG. 15 is a flowchart illustrating a procedure of a body fluid measurement specimen preparing process.

FIG. 15 is a flowchart illustrating a procedure of a body fluid measurement specimen preparing process. In the body fluid measurement specimen preparing process, the microcomputer 11 first controls the sample distributing section 1 to cause the aspirating tube 17 to aspirate a predetermined amount of body fluid sample from the test tube T and dispense aliquots of the predetermined amount of body fluid sample to the reaction chamber 2u and the reaction chamber 2b (steps S601, S602).

A predetermined amount of first reagent 19u and third reagent 18u are quantified and dispensed to the reaction chamber 2u (step S603 and step S604). Similarly, a predetermined amount of second reagent 19b and fourth reagent 18b are quantified and dispensed to the reaction chamber 2b (step S605 and step S606). The reaction chamber 2u and the reaction chamber 2b are respectively warmed to a predetermined temperature by a heater (not shown), and the mixture is stirred with a stirring tool (not shown) having a propeller (step S607). Thus, the BF-RBC for the red blood cell measurement is prepared in the reaction chamber 2u, and the BF-WBC for measuring nucleated cell/bacteria is prepared in the reaction chamber 2b. After the process of step S607 is finished, the microcomputer 11 returns the process to the main routine.

The amount of body fluid sample, the amount of first reagent 19u, and the amount of third reagent 18u supplied to the reaction chamber 2u in steps S601, S603, and S604 are the same as the amount of urine sample, the amount of first reagent 19u, and the amount of third reagent 18u supplied to the reaction chamber 2u in steps S301, S303, and S304. The amount of body fluid sample, the amount of second reagent 19b, and the amount of fourth reagent 18b supplied to the reaction chamber 2b in steps S602, S605, and S606 are the same as the amount of urine sample, the amount of second reagent 19b, and the amount of fourth reagent 18b supplied to the reaction chamber 2u in steps S302, S305, and S306. That is, BF-RBC is prepared under the same condition (amount of sample, as well as type and amount of stain fluid and diluent) as the U-SED, and the BF-WBC is prepared under the same condition (amount of sample, as well as type and amount of stain fluid and diluent) as the U-BAC.

FIG. 16 is a flowchart illustrating a procedure of the red blood cell measurement process. In the red blood cell measurement process, the microcomputer 11 first sets the sensitivity of the FSC detector 55, the SSC detector 58, and the FL detector 59, and the gain of the amplification circuit 50 with the third set value for the red blood cell measurement (step S701). The microcomputer 11 then causes the compressor 22a to supply the compressed air to the sheath fluid accommodating portion 22 to feed the sheath fluid to the sheath flow cell 51 (step S702). The BF-RBC is supplied from the reaction chamber 2u to the sheath flow cell 51 while the supply of sheath fluid to the sheath flow cell 51 is continued (step S703).

The process of step S703 differs from the process of step S403 in the push-out amount per unit time of the syringe pump 20b. That is, in the process of step S703, the syringe pump 20b is driven at the push-out amount per unit time defined for BF-RBC measurement. The BF-RBC between the electromagnetic valve 21c and the electromagnetic valve 21d is pushed out toward the sheath flow cell 51. The push-out amount per unit time for the BF-RBC measurement is ⅛ of the push-out amount per unit time for the urine sediment measurement.

Figure 17A:
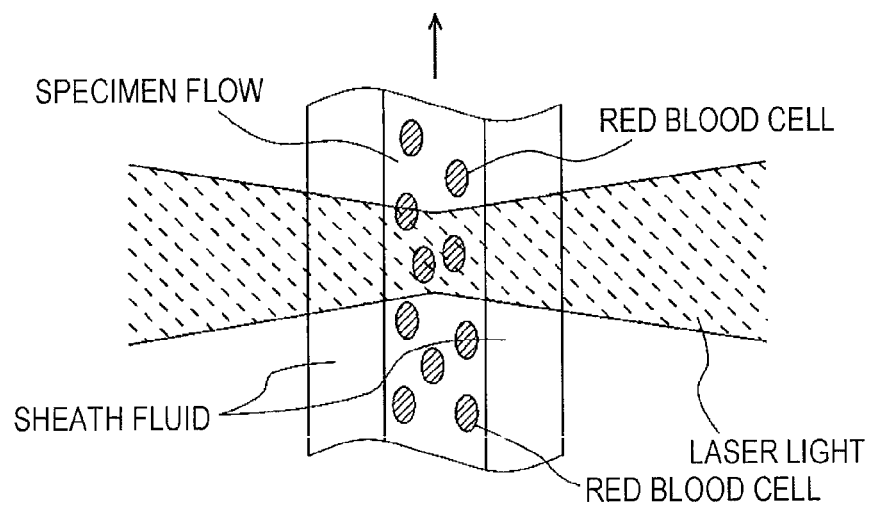
FIG. 17A is a schematic view illustrating a sheath flow of BF-RBC formed under the same condition as when measuring the urine sediment.
Figure 17B:
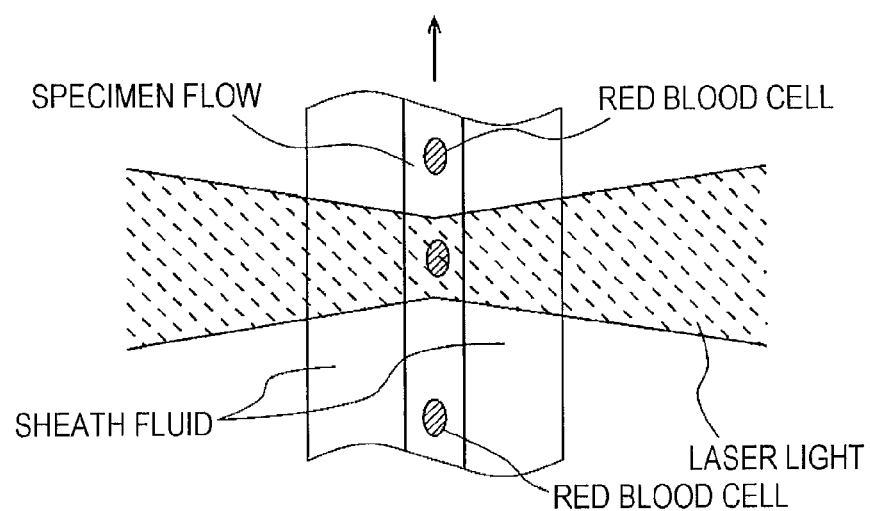
FIG. 17B is a schematic view illustrating a sheath flow of the BF-RBC under the condition for the red blood cell measurement in the body fluid.

FIG. 17A is a schematic view of when the sheath flow of the BF-RBC is formed under the same condition for U-SED, and FIG. 17B is a schematic view of when the sheath flow of the BF-RBC is formed under the dedicated condition for the BF-RBC. Compared to urine, the body fluid tends to have high concentration of red blood cells. Hence if the flow of the BF-RBC is formed under the same push-out amount per unit time condition, two or more red blood cells may simultaneously pass through the beam spot of the laser light, due to the high concentration of red blood cells. It may cause inaccurate counting of red blood cells (see FIG. 17A). On the contrary, if the push-out amount per unit time is reduced, the flow of the BF-RBC can be more diluted and narrowed. It makes possible to flow red blood cells separately to pass through the beam spot one by one. Inaccurate counting is prevented (see FIG. 17B).

Figure 18:
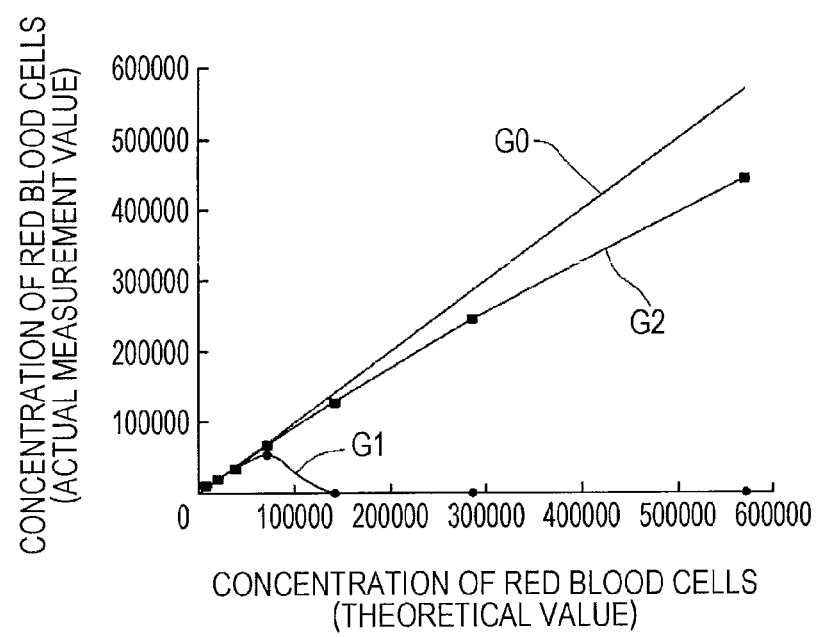
FIG. 18 is a graph illustrating a relationship of a feeding amount per unit time of the BF-RBC and a counted value.

FIG. 18 is a graph illustrating a relationship of a feeding amount per unit time of the BF-RBC and a counted value. In the figure, G0 indicates a theoretical value, G1 indicates the counted value of when the BF-RBC is fed at the feeding amount per unit time same as the condition for U-SED. G2 indicates the counted value of when the BF-RBC is fed at the feeding amount per unit time of ⅛ of when measuring the urine sediment. The vertical axis indicates the counted value of the actual measurement, and the horizontal axis indicates the theoretical value. As shown in the figure, when the BF-RBC is fed at the same condition for the U-SED, the actual measurement value corresponds to the theoretical value up to the concentration of about 70 thousand/μL, but reaches the peak at about 70 thousand/μL, and reduces thereafter. This is assumed to be because the frequency at which the red blood cells simultaneously pass increases as the concentration of the red blood cells increases, as shown in FIG. 17A. If, on the other hand, the BF-RBC is fed at the feeding amount per unit time of ⅛ of the condition for U-SED, the actual measurement value corresponds to the theoretical value up to the high concentration, and accurate counting can be carried out.

Other operations in the process of step S703 are similar to the operations described in the process of step S403, and thus the description thereof will be omitted.

The sheath flow is irradiated with the laser beam from the laser light source 53 (step S704), so that the forward scattered light, the fluorescence light, and the side scattered light of the red blood cells are generated. The forward scattered light, the fluorescence light, and the side scattered light are respectively received by the FSC detector 55, the FL detector 59, and the SSC detector 58 and converted to the electric signal (step S705). The supply of the BF-RBC to the sheath flow cell 51 and detection of signals in step S705 are carried out for a time determined in advance for the BF-RBC measurement. The measurement time of BF-RBC is the same as the measurement time for the U-SED.

The electric signals corresponding to the light receiving levels of the FSC detector 55, the FL detector 59, and the SSC detector 58 are output as the forward scattered light signal (FSC), the first fluorescence signal (FLH), the second fluorescence signal (FLL) and the side scattered light signal (SSC). Such output signals are amplified by the amplification circuit 50. In this case, the signals are output from the FSC detector 55, the FL detector 59, and the SSC detector 58 at the sensitivity defined by the third set value for the red blood cell measurement set in step S701, and the output signals of the FSC detector 55, the FL detector 59, and the SSC detector 58 are amplified by the amplification circuit 50 at the amplification rate defined by the third set value. The sensitivity set values of the FSC detector 55 and the SSC detectors 58, 59 at the third set value are all low sensitivity, and are the same as the sensitivity set values at the first set value. The gain set value of the amplification circuit 50 at the third set value is the same as the gain set value of the amplification circuit 50 at the first set value. Therefore, when the third set value is set, signals of the forward scattered light, side scattered light, fluorescence, are amplified under the same conditions as the state in which the first set value is set, and the signals are output from the amplifier circuit 50.

The amplified forward scattered light signal (FSC), the fluorescence signal (FL), and the side scattered light signal (SSC) are filtered by the filter circuit 6, converted to digital signals by the A/D converter 7, processed by the digital signal processing circuit 8, and stored in the memory 9 as measurement data (step S706). After the above processes are completed, the microcomputer 11 returns the process to the main routine.

Figure 19:
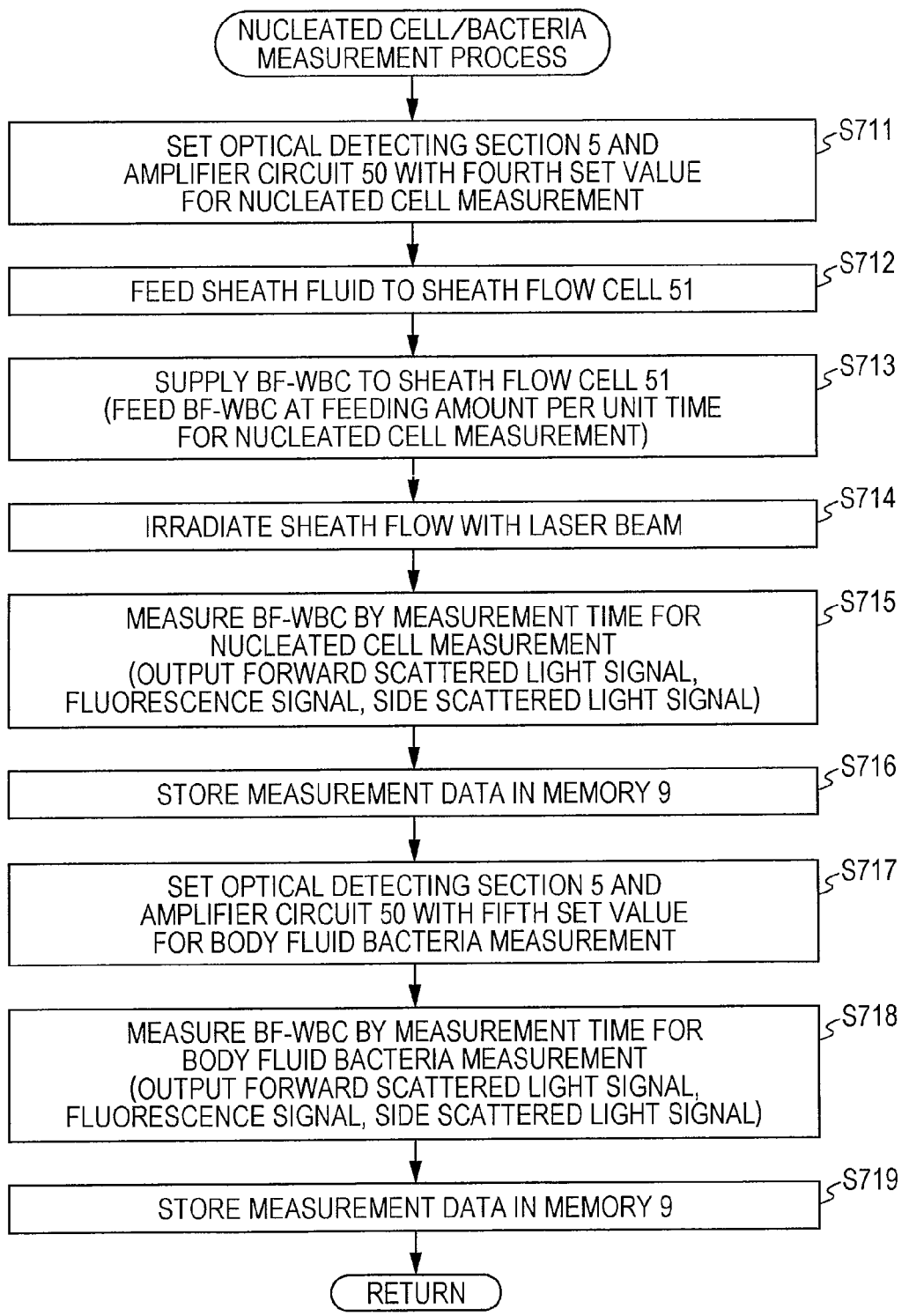
FIG. 19 is a flowchart illustrating a procedure of a measurement process of nucleated cells and bacteria in the body fluid.

FIG. 19 is a flowchart illustrating a procedure of the nucleated cell/bacteria measurement process. In the nucleated cell/bacteria measurement process, the microcomputer 11 first sets the sensitivities of the FSC detector 55, the SSC detector 58, and the FL detector 59 and the gain of the amplification circuit 50 at the fourth set value for the BF-WBC measurement (step S711). The microcomputer 11 then causes the compressor 22a to supply the compressed air to the sheath fluid accommodating portion 22 to feed the sheath fluid to the sheath flow cell 51 (step S712). The BF-WBC is supplied from the reaction chamber 2b to the sheath flow cell 51 while the supply of sheath fluid to the sheath flow cell 51 is continued (step S713).

The process of step S713 is similar to the process of step S413, and thus the description thereof will be omitted. In step S713, the syringe pump 20b is driven at the feeding amount per unit time same as the condition for the U-BAC.

In the process of step S713, flow of the BF-WBC diluted and enveloped by the sheath fluid is formed in the sheath flow cell 51. The flow of BF-WBC is irradiated with the laser beam from the laser light source 53 (step S714), so that the forward scattered light, the fluorescence light, and the side scattered light are generated. The forward scattered light, the fluorescence light, and the side scattered light are respectively received by the FSC detector 55, the FL detector 59, and the SSC detector 58 and converted to the electric signal (step S715). The supply of the BF-WBC to the sheath flow cell 51 and detection of signals in step S715 are carried out for a time determined in advance for the nucleated cell measurement on the BF-WBC. This measurement time for the nucleated cell measurement on the BF-WBC is longer than the measurement time for the U-BAC. The concentration of white blood cells in the body fluid is extremely low or about a few number per 1 µL. In some cases, a sufficient number of white blood cells for performing an accurate analysis are not detected if the measurement time is the same as the measurement time for the U-BAC measurement, due to low concentration of white blood cells in body fluid. Thus, the measurement time for the nucleated cells measurement on the BF-WBC is longer than the measurement time for the U-BAC in order to increase the volume of the BF-WBC to be analyzed. It enables the measurement of white blood cells in the body fluid at high accuracy.

The electric signals corresponding to the light receiving level of the FSC detector 55, the FL detector 59, and the SSC detector 58 are output as the forward scattered light signal (FSC), the first fluorescence signal (FLH), the second fluorescence signal (FLL) and the side scattered light signal (SSC). Such output signals are amplified by the amplification circuit 50. In this case, the signals are output from the FSC detector 55, the FL detector 59, and the SSC detector 58 at the sensitivity defined by the fourth set value for the BF-WBC measurement set in step S711, and the output signals of the FSC detector 55, the FL detector 59, and the SSC detector 58 are amplified by the amplification circuit 50 at the amplification rate defined by the fourth set value. The sensitivity set values of the FSC detector 55, the SSC detector 58, and the FL detector 59 at the fourth set value are all low sensitivities. The sensitivities of the FSC detector 55, the SSC detector 58, and the FL detector 59 set by the fourth set value are much less than the sensitivities set by the second set value for the U-BAC. More specifically, the sensitivity of the forward scattered light signal for measuring nucleated cells in the BF-WBC when the fourth set value is set is less than 1/10 of the sensitivity of the forward scattered light signal for the U-BAC measurement (the second set value), and is the same as the sensitivity of the forward scattered light for the U-SED measurement (the first set value). Furthermore, the sensitivity of the fluorescence signal for measuring nucleated cells in the BF-WBC measurement when the fourth set value is set is a fraction of the sensitivity of the fluorescence signal for the U-BAC measurement (the second stet value), and is almost same with the sensitivity of when the first set value is set. This is because the nucleated cell (white blood cells and large cells) has a large size compared to the bacteria, and causes high scattered light intensity and high fluorescence intensity compared to bacteria. That is, sensitivity suited for the nucleated cell is realized and the nucleated cell in the body fluid can be detected at high accuracy by making the sensitivities of the FSC detector 55, the SSC detector 58, and the FL detector 59 lower than the sensitivity for the U-BAC measurement.

The amplified forward scattered light signal (FSC), the fluorescence signal (FL), and the side scattered light signal (SSC) are filtered by the filter circuit 6, converted to digital signals by the A/D converter 7, processed by the digital signal processing circuit 8, and stored in the memory 9 as measurement data (step S716).

After the measurement time for the nucleated cells measurement on the BF-WBC elapses, the microcomputer 11 sets the sensitivities of the FSC detector 55, the SSC detector 58, and the FL detector 59 and the gain of the amplification circuit 50 at the fifth set value for the bacteria measurement in the body fluid (step S717), during supplying the sheath fluid and the BF-WBC to the sheath flow cell 51. The forward scattered light, the fluorescence, and the side scattered light generated from the BF-WBC are respectively received by the FSC detector 55, the FL detector 59, and the SSC detector 58 and converted to electric signals (step S718). The sensitivity set values of the FSC detector 55, the SSC detector 58, and the FL detector 59 at the fifth set value are all high sensitivities. The sensitivities of the FSC detector 55, the SSC detector 58, and the FL detector 59 set by the fifth set value are the same as the sensitivities of the FSC detector 55, the SSC detector 58, and the FL detector 59 set by the second set value for the bacteria measurement on the U-BAC. The bacteria in the body fluid thus can be detected at high accuracy according to the characteristics thereof. The measurement data is stored in the memory (step S719).

After the above processes are completed, the microcomputer 11 returns the process to the main routine.

After the nucleated cell/bacteria measurement process described above, the microcomputer 11 transmits the measurement data generated by the red blood cell measurement process and the nucleated cell/bacteria measurement process to the information processing unit 13 (step S507), and terminates the process.

When the information processing unit 13 receives the measurement data (step S508), the CPU 401 executes an analyzing process of the measurement data (step S509), generates an analysis result of the body fluid sample, and stores the analysis result in the hard disk 404.

In the analyzing process of step S509, red blood cells (RBC) in body fluid are detected and counted from the measurement data of the BF-RBC. Specifically, the red blood cells (RBC) are classified from other particles and counted based on the intensity of the forward scattered light signal (FSC-3) and the intensity of the first fluorescence signal (FLH-3). In other words, the red blood cells in the body fluid are detected based on the forward scattered light intensity and the fluorescence intensity, which are the same parameters used for the detection of red blood cells in the urine. The drawing data for drawing a fifth distribution diagram in which red blood cells in the body fluid are plotted at coordinates according to the intensity of the forward scattered light signal (FSC-3) and the intensity of the first fluorescence signal (FLH-3) of the measurement result of the BF-RBC is also generated.

In the analyzing process of step S509, the nucleated cells (TNC) and the bacteria (BACT) in the body fluid are detected and counted from the measurement data of the BF-WBC. The nucleated cells (TNC) are classified to the white blood cells (WBC) and the large cells (LC) and the respective cells are counted. Specifically, the nucleated cells (TNC) are classified from other particles and counted based on the intensity of the forward scattered light signal (FSC-4) and the intensity of the first fluorescence signal (FLH-4). The bacteria are classified from other particles and counted based on the intensity of the forward scattered light signal (FSC-5) and the intensity of the first fluorescence signal (FLH-5). Furthermore, drawing data for drawing a sixth distribution diagram in which nucleated cells of BF-WBC are plotted at coordinates according to the intensity of the forward scattered light signal (FSC-4) and the intensity of the first fluorescence signal (FLH-4) of the measurement result of the BF-WBC is generated. And drawing data for drawing a seventh distribution diagram in which the bacteria of the BF-WBC are plotted at positions according to the intensity of the forward scattered light signal (FSC-5) and the intensity of the first fluorescence signal (FLH-5) of the measurement result of the BF-WBC is generated.

The classification of white blood cells (WBC) and large cells (LC) described above is carried out in the following manner. Among the measurement data of the BF-WBC obtained in step S715, red blood cell ghosts (destroyed red blood cells), bacteria, crystals, and other particles appear in the low value region of the fluorescence intensity and the forward scattered light intensity, and a group of nucleated cells including white blood cells and large cells appears in the portion excluding the above regions. The measurement data appears at the region other than the low value region are extracted as the group of nucleated cells. The extracted data are classified into two groups when a histogram of the extracted data is made according to the pulse width of the forward scattered light signal. This is because the white blood cells and the large cells have different sizes. White blood cells are smaller. And the pulse width of the forward scattered light signal accurately reflects the size of the cell. Thus, in the analyzing process of step S509, the white blood cells and the large cells are classified from the pulse width of the forward scattered light signal contained in the extracted data.

The CPU 401 then displays the analysis result obtained in the above manner on the display unit 409 (step S510), and terminates the process.

Figure 20:
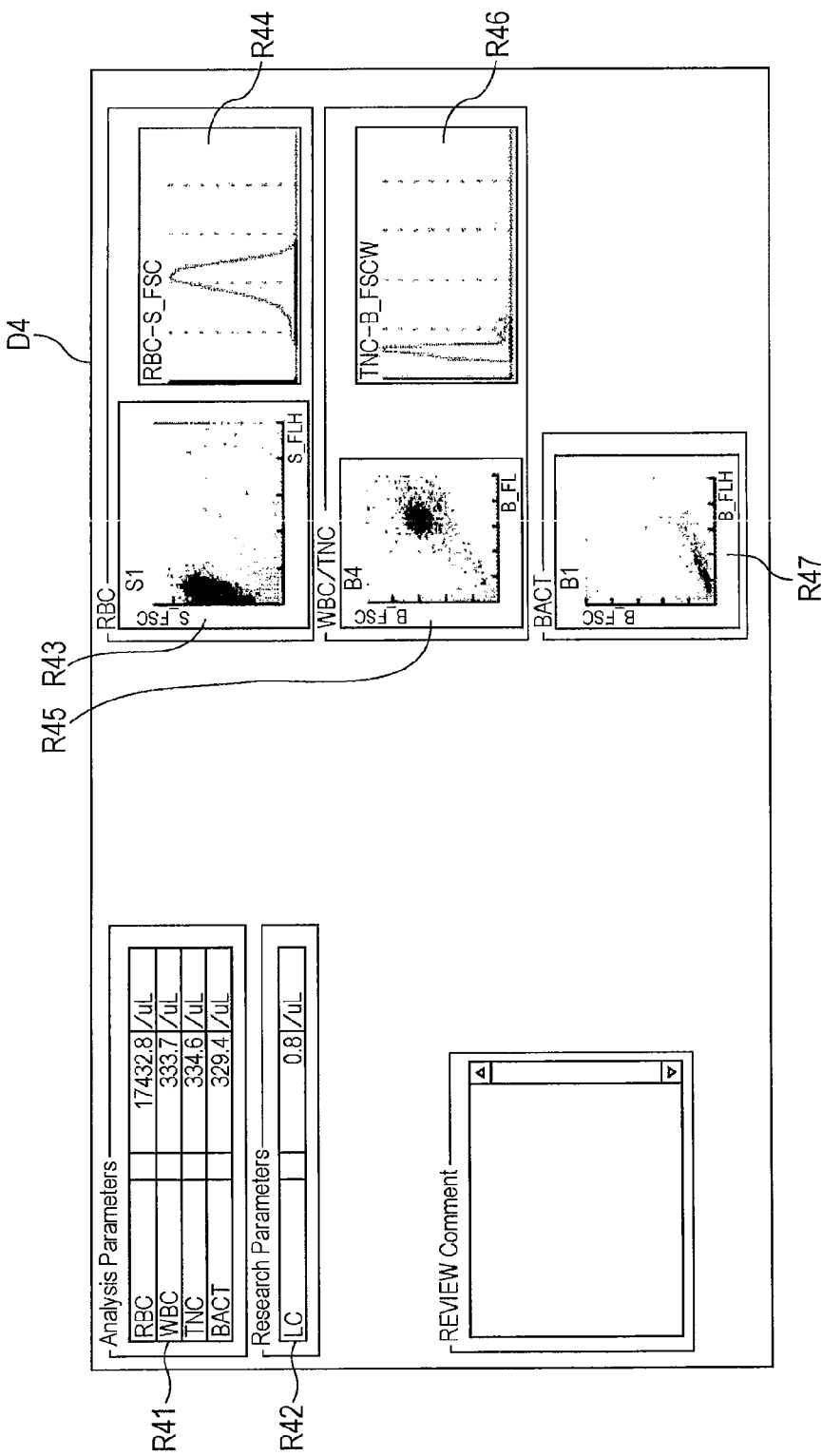
FIG. 20 is a view illustrating an analysis result screen of the body fluid sample.

FIG. 20 is a view illustrating an analysis result screen of the body fluid sample. As shown in the figure, a body fluid sample analysis result screen D4 includes an analysis parameter section R41, which displays counts of red blood cells, white blood cells, and nucleated cells as well as bacteria. The screen D4 also includes a research parameter section R42, which displays a count of large cells, the fifth distribution diagram R43, a histogram R44 of the red blood cells according to the forward scattered light intensity, the sixth distribution diagram R45, a histogram R46 of the nucleated cells according to the pulse width of the forward scattered light intensity, and the seventh distribution diagram R47.

OTHER EMBODIMENTS

In the embodiment described above, the configuration of measuring the urine sediment such as red blood cells and white blood cells from the U-SED and measuring the bacteria from the U-BAC in the urine measurement mode has been described. That is, in the above embodiment, two measurement specimens are prepared from urine sample. One is prepared for sediments, the other is prepared for bacteria. However, configuration of the analyzer is not limited to the above described mode. The two measurement specimens prepared in the urine measurement mode may not be distinguished as one for sediments and the other for bacteria. For example, one measurement specimen may be used to measure the nucleated cells (white blood cells, epidermal cells, etc.) and the other measurement specimen may be used to measure the anucleate cells (red blood cells, casts. etc.).

Urine sample analyzer of another embodiment will be described below. The analyzer is operable, under urine measurement mode, to prepare a first measurement specimen in which cell membranes and proteins of urinary sediments are stained by mixing a urine sample, a first regent free from a hemolytic effect and a third reagent for staining cell membranes and proteins. The analyzer is operable to measure anucleate cells including red blood cells and casts in the first measurement specimen. Further the analyzer is operable, under the urine measurement mode, to prepare a second measurement specimen in which nucleic acid of nucleate cells are stained by mixing a urine sample, a second regent having a hemolytic effect and a fourth reagent for staining nucleic acid. The analyzer is operable to measure nucleated cells including white blood cells in the second measurement specimen. In this embodiment, under body fluid measurement mode, the analyzer prepares a third measurement specimen in which cell membranes of anucleate cells, at least red blood cells, in body fluid are stained by use of the first and third reagents employed for the anucleate cells in urine. The analyzer measures red blood cells in body fluid from the third measurement specimen. Further, under body fluid measurement mode, the analyzer prepares a fourth measurement specimen in which nucleic acid of nucleated cells, at least white blood cells, in body fluid are stained by use of the second and fourth reagents employed for the nucleated cells in urine. The analyzer measures white blood cells in body fluid from the fourth measurement specimen.

Figure 21:
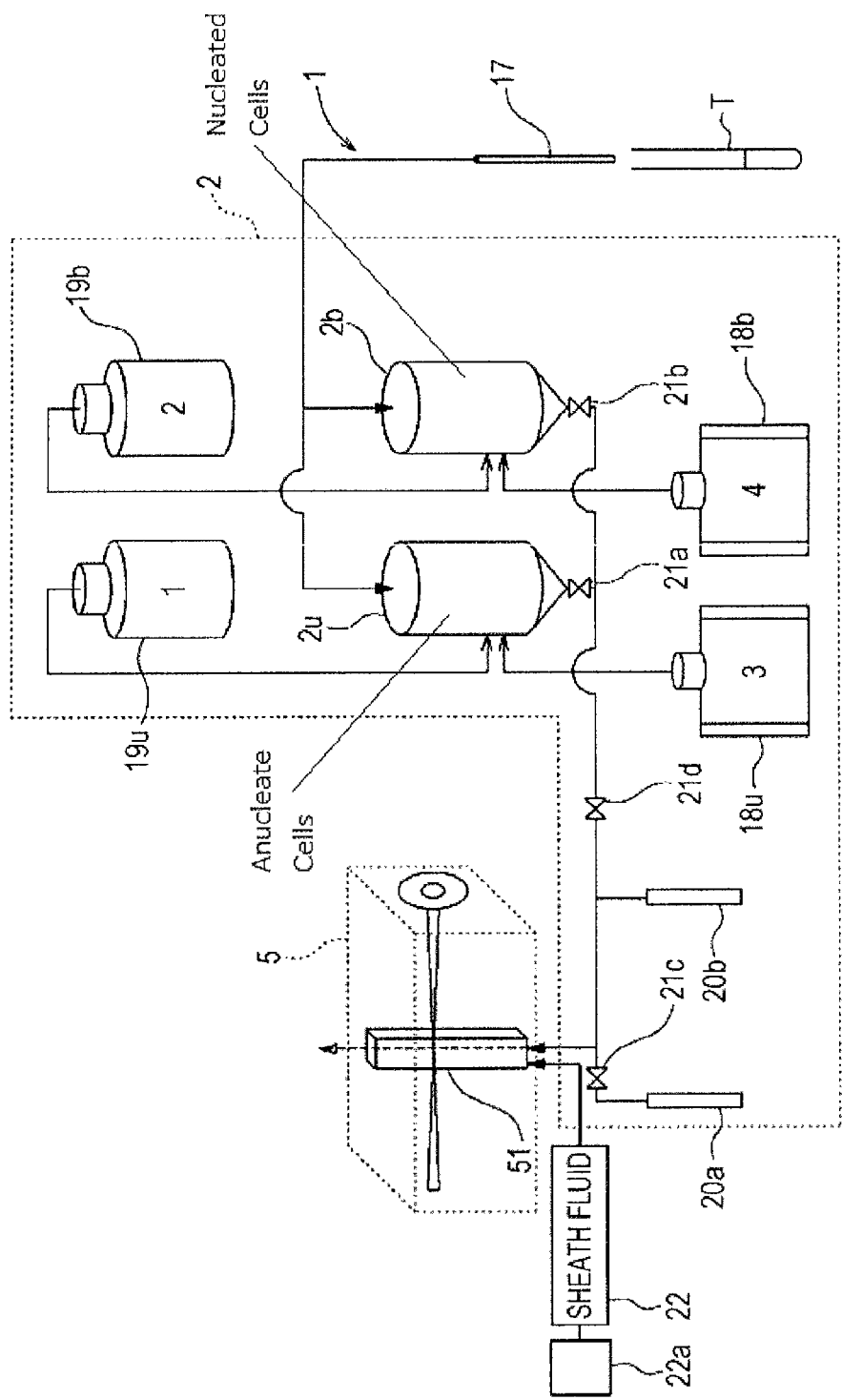
FIG. 21 is a schematic diagram illustrating a configuration of the urine sample analyzer of another embodiment.

FIG. 21 is a schematic diagram illustrating a configuration of the urine sample analyzer of another embodiment as described above. The main structure of the urine sample analyzer 1 is the same as the embodiment described above.

The analyzer is equipped with a first reagent 19u containing a diluent for anucleate cells, and a second reagent 19b containing a diluent of nucleated cells, a third reagent 18u containing the dye for staining anucleate cells and a fourth reagent 18b containing a dye for staining nucleated cells.

The first reagent 19u is a buffer solution containing a buffering agent as its main component. The first reagent 19u contains osmotic pressure compensating agent to make cells suitably be stained by the third reagent 18u without lysing red blood cells. The osmotic pressure of the first reagent 19u is adjusted not to lyse red blood cells in urine, particularly in the range of 100 to 600 mOsm/kg so that classification measurements of urinary sediments are suitably performed. The first reagent 19u is free from a hemolytic agent having a hemolytic effect on red blood cells in urine as with the embodiment described above.

As with the embodiment described above, the second reagent 19b has a hemolytic effect. More specifically, the second reagent 19b contains a cationic surfactant for enhancing a staining by the fourth reagent 18b by damaging the cell membrane, hemolyzing erythrocytes and shrinking contaminants erythrocyte debris. As with the embodiment described above, instead of containing a surfactant, the second reagent 19b may acquire hemolytic effect by being adjusted its osmotic pressure and/or pH.

The third reagent 18u contains a dye for staining proteins and cell membranes, and is used to measure anucleate cells such as red blood cells, casts, mucus, crystals in urine. As the dye, a dye having a staining effect to cell membrane is preferably selected. Preferably, the dye which does not affect the morphology of red blood cells is selected among cyanine dye, styryl dye, or acridine dye. Lipophilic carbocyanine dyes are preferably used. Indocarbocyanine dyes, oxacarbocyanine dyes are particularly preferred.

The fourth reagent 18b contains dye for specifically staining nucleic acid, and is used to measure nucleated cells such as white blood cells, epithelial cells, fungi, bacteria. To be more specific, in the fourth reagent 18b, intercalator or a dye that binds to a minor groove is contained. As examples of the intercalator, known cyanine dyes, acridine dyes, or phenanthridium dyes are mentioned.

In the urine measurement mode, the reaction chamber 2u mixes the first reagent 19u, third reagent 18u and urine sample. Thus, the first measurement specimen is prepared, in which cell membranes or proteins of anucleate cells in urine are stained and morphologies of red blood cells in urine are maintained. The first measurement specimen is fed to the optical detector 5 as in the embodiment described above, and then the detection of signals of anucleate cells such as red blood cells in urine are performed.

In urine measurement mode, the reaction chamber 2b mixes the second reagent 19b, the fourth reagent 18b and urine sample. Thus, the second measurement specimen is prepared, in which nucleated cells having nucleic acids in urine are stained and red blood cells in urine are lysed. The second measurement specimen is fed to the optical detector 5 as in the embodiment described above, and then the detection of signals of the nucleated cells such as white blood cells, epithelial cells, fungi, and bacteria in urine are performed.

In the body fluid measurement mode, the reaction chamber 2u mixes the first reagent 19u, the third reagent 18u and body fluid sample. Thus, the third measurement specimen is prepared, in which cell membranes or proteins of anucleate cells in body fluid are stained and morphologies of red blood cells in body fluid are maintained. The third measurement specimen is fed to the optical detector 5 as in the embodiment described above, and then the detection of signals of anucleate cells such as red blood cells in body fluid are performed.

In the body fluid measurement mode, the reaction chamber 2b mixes the second reagent 19b, the fourth reagent 18b and body fluid sample. Thus, the fourth measurement specimen is prepared, in which nucleated cells having nucleic acids in body fluid are stained and red blood cells in body fluid are lysed. The fourth measurement specimen is fed to the optical detector 5 as in the embodiment described above, and then the detection of signals of the nucleated cells such as white blood cells and bacteria in body fluid are performed.

Furthermore, in the embodiment described above, the configuration of optically measuring the components in urine or body fluid by flow cytometry that uses a flow cell and light receiving elements has been described, however the configuration is not limited to this embodiment. For example, the components in urine or body fluid may be measured by applying voltage to the flow cell and detecting change of voltage when component passes the floe cell. In this case, the components do not need to be dyed, and hence the dyeing reagent can be saved. Moreover, the optical information other than fluorescence such as scattered light, absorbance, and the like may be used even in the flow cytometry. In this case as well, the components do not need to be dyed, and hence the dyeing reagent can be saved.

In the embodiment described above, the diluent such as the first reagent 19u and the dyeing reagent such as the third reagent 18u are separate solutions, but they may be combined to one solution.

In the embodiment described above, the feeding amount per unit time of the measurement specimen to the flow cell differs between when measuring the urine sediment and when measuring the red blood cells in the body fluid. However, it is not limited to this embodiment. They may be same between the two measurement modes. For example, by increasing amount of the first reagent 19u to be mixed with body fluid in the reaction chamber 2u, the dilution magnification of the body fluid in the BF-RBC may be adjusted higher than the dilution magnification of the urine sample in the U-SED. In this case, the feeding amount per unit time to the flow cell may be set the same for the U-SED and the BF-RBC. Both the dilution magnification and the feeding amount per unit time may be differed between when measuring the urine sediment and when measuring the red blood cells in the body fluid. In such case as well, the simultaneous passing of red blood cells in the flow cell can be prevented.

In the embodiment described above, the sensitivities of the FSC detector 55, the SSC detector 58, and the FL detector 59 and the gain of the amplification circuit 50 are differed between when measuring the bacteria in the urine and when measuring the nucleated cells in the body fluid, but it is not limited to the embodiment. Only the gain of the pre-amplifier connected to each light receiving element of the FCM section 5 may be differed between when measuring the bacteria in the urine and when measuring the nucleated cells in the body fluid. In this case, the gain of the amplification circuit 50 does not need to be changed between when measuring the bacteria in the urine and when measuring the nucleated cells in the body fluid. The gains of both the pre-amplifier and the amplification circuit 50 may be differed between when measuring the bacteria in the urine and when measuring the nucleated cells in the body fluid. Only the sensitivity of each light receiving element may be switched between when measuring the bacteria in the urine and when measuring the nucleated cells in the body fluid, and the gains of the pre-amplifier and the amplification circuit 50 may be fixed. Accordingly, the sensitivities of the forward scattered light signal, the side scattered light signal, and the fluorescence signal can be changed according to the measurement mode.

In the embodiment described above, the configuration capable of analyzing the urine sample and the body fluid sample has been described, but it is not limited to this embodiment. A configuration capable of measuring the blood sample (whole blood sample) instead of the body fluid sample may be adopted. Since the blood sample contains a great amount of red blood cells, the nucleated cells can be accurately measured by performing the measurement after performing hemolytic process on the blood sample when measuring the nucleated cells such as the white blood cells, and the like in the blood sample.

Further, the amount of aspirating sample in the urine measurement mode may be differed from the amount of aspirating sample in the body fluid measurement mode in the embodiment as described above. Since body fluid is difficult to be collected than urine, the amount of aspirating sample in the body fluid measurement mode is preferably less than that of the urine measurement mode.

Further, in the above described embodiment, since the third measurement specimen in the body fluid measurement mode is prepared in same manner as the first measurement specimen in the urine measurement mode, the third measurement specimen and the first measurement specimen are prepared in the same amount. However, since an amount of the third measurement specimen required for analysis is less than the first measurement specimen, preparation amount of the third measurement specimen may be less than the that of the first measurement specimen. Amount of the preparation of third measurement specimen may be reduced to an amount necessary to performing measurement by the optical detector. Since feed amount of the syringe pump per unit time of the third measurement specimen is ⅛ of the first measurement specimen and the measurement time is the same as the first measurement specimen, necessary amount of the third measurement specimen is ⅛ of the first measurement specimen. Thus, in the body fluid measurement mode, the amount of body fluid sample dispensed by the sample distributing section 1 to the reaction chamber 2u and the amounts of the first and third reagents dispensed to the reaction chamber 2u may respectively be adjusted to ⅛ than the urine sample measurement mode. Thus, the amount of body fluid sample to be aspirated and reagents consumption can be reduced.

If the preparation of the third measurement specimen is reduced in the body fluid measurement mode, by increasing the preparation of the fourth measurement specimen alternatively, the measurement time of the fourth measurement specimen may be longer. By increasing the amount of the fourth measurement specimen to be measured, it is possible to improve the accuracy of the counting of white blood cells. In this case, the amount of body fluid dispensed by the sample distributing section 1 to the reaction chamber 2u is reduced, and larger amount of body fluid is dispensed to the reaction chamber 2b.

In another embodiment, the measurement time of the fourth measurement specimen may be variable in accordance with the measurement result of the third measurement specimen. FIG. 22 is a modification of the flowchart of the measurement unit side in FIG. 14. After the red blood cell measurement process in S505 is performed, the microcomputer 11 determines whether the number of measurement data of particles input from the digital signal processing circuit 8 is equal to or more than the threshold value (step S5051). If the number of the measurement data is equal to or larger than the threshold value, the body fluid sample likely contains plenty of red blood cells and is contaminated with blood. In this case, the body fluid sample likely contains plenty of white blood cells, and even without increasing the measurement time of the fourth measurement specimen, sufficient number of white blood cells can be measured. Therefore, the microcomputer 11 continues the process to the S5061 if the number of measurement data is equal to or greater than the threshold value, and performs the nucleated cells/bacteria measurement process of the fourth measurement specimen by reducing the measurement time (step S5061). In this case, the measurement time of the fourth measurement specimen may be 1 to 3 times of the measurement time of the second measurement specimen in urine measurement mode.

On the other hand, if the number of the measurement data is less than the threshold value, since the concentration of white blood cells is low, the nucleated cells/bacteria measurement process of the fourth measurement specimen is performed for a longer time than the measurement time in the S5061 (step S506). Specifically, the measurement time in the S5061 may be 6 times of the measurement time of the second measurement specimen in the urine measurement mode.

The invention claimed is:

1. A urine analyzer capable of operating in a urine measurement mode and a body fluid measurement mode, the urine analyzer comprising:
   a specimen preparing section configured to prepare a measurement specimen;
   a detecting section configured to derive signals of particles in the measurement specimen supplied from the specimen preparing section; and
   a computer and a memory storing programs that enable the computer to execute operations comprising:

(A) in the urine measurement mode,
      control the specimen preparing section to prepare a first measurement specimen by mixing a first aliquot of a urine sample and a first reagent, to prepare a second measurement specimen by mixing a second aliquot of the urine sample and a second reagent having a hemolytic effect, and to supply the first and second measurement specimens to the detecting section; and
      analyze the signals of the first measurement specimen to measure red blood cells in the urine sample and analyze the signals of the second measurement specimen to measure bacteria in the urine sample,
   (B) in the body fluid measurement mode,
      control the specimen preparing section to prepare a third measurement specimen by mixing a first aliquot of body fluid sample and the first reagent, to prepare a fourth measurement specimen by mixing a second aliquot of body fluid sample and the second reagent, and to supply the third and fourth measurement specimens to the detecting section; and
      analyze the signals of the third measurement specimen to measure red blood cells in the body fluid sample and analyze the signals of the fourth measurement specimen to measure white blood cells in the body fluid sample,
   wherein the body fluid sample does not include a blood sample, a urine sample, or a lymph fluid sample.

2. The urine analyzer according to claim 1, wherein the programs further enable the computer to analyze the signals of the fourth measurement specimen to further measure nucleated cells different from the white blood cells.

3. The urine analyzer according to claim 1, wherein the specimen preparing section is configured to, under the control of the computer,
   prepare the first measurement specimen by mixing the first aliquot of the urine sample, the first reagent, and a third reagent for dyeing cell membranes,
   prepare the second measurement specimen by mixing the second aliquot of the urine sample, the second reagent, and a fourth reagent for dyeing nucleic acid,
   prepare the third measurement specimen by mixing the first aliquot of the body fluid sample, the first reagent, and the third reagent, and
   prepare the fourth measurement specimen by mixing the second aliquot of the body fluid sample, the second reagent, and the fourth reagent.

4. The urine analyzer according to claim 1, wherein the programs further enable the computer to
   control the preparation of the first measurement specimen or supply the first measurement specimen to the detecting section by the specimen preparing section according to a first measurement condition, and
   control the preparation of the third measurement specimen or supply the third measurement specimen to the detecting section by the specimen preparing section according to a second measurement condition different from the first measurement condition.

5. The urine analyzer according to claim 4, wherein the programs further enable the computer to control the preparation or supply of the third measurement specimen by the specimen preparing section, according to the second measurement condition, so that the dilution magnification of the body fluid sample when the signal of the particles in the third measurement specimen is detected by the detecting section is higher than the dilution magnification of the urine sample when the signal of the particles in the first measurement specimen is detected by the detecting section.

6. The urine analyzer according to claim 5, wherein the sample preparation portion is configured to supply the measurement specimens to the detecting section with a diluent, the programs further enable the computer to control the specimen preparing section to:

supply the first measurement specimen with the diluent of a first volume under the first measurement condition, and supply the third measurement specimen with the diluent of a second volume greater than the first volume under the first measurement condition.

7. The urine analyzer according to claim 5, wherein the programs further enable the computer to control the specimen preparing section to:

prepare the first measurement specimen in which the urine sample is diluted and supply the first measurement specimen to the detecting section under the first measurement condition, prepare the third measurement specimen in which the body fluid sample is diluted in a greater dilution magnification than the first measurement condition and supply the third measurement specimen to the detecting section under the second measurement condition.

8. The urine analyzer according to claim 4, wherein the detecting section includes a flow cytometer for irradiating a flow of the measurement specimen running in a flow cell with a beam of light, and the programs further enable the computer to control, under the second measurement condition, the specimen preparing section to make the flow of the third measurement specimen narrower than under the first measurement condition.

9. The urine analyzer according to claim 8, wherein the specimen preparing section is capable of supplying the measurement specimen into the flow cell while flowing the diluent into the flow cell, the programs further enable the computer to, under the second measurement condition, control the specimen preparing section so that the amount of third measurement specimen supplied to the flow cell per unit time is decreased than the amount of first measurement specimen supplied to the flow cell per unit time under the first measurement condition.

10. The urine analyzer according to claim 6, wherein the detecting section is configured to, under the control of the computer, derive signals from the third measurement specimen under a third measurement condition, and derive signals from the fourth measurement specimen under a fourth measurement condition different from the third measurement condition.

11. The urine analyzer according to claim 10, wherein the detecting section is configured to adjust a detection sensitivity; and the detection sensitivity applied in the third measurement condition is higher than the detection sensitivity in the fourth measurement condition.

12. The urine analyzer according to of claim 1, wherein the detecting section is configured to, under the control of the computer, detect signals of particles in a part of the fourth measurement specimen in a first detection sensitivity, and detect signals of particles in another part of the fourth measurement specimen in a second detection sensitivity higher than the first detection sensitivity, and the programs further enable the computer to measure white blood cells in the body fluid sample by analyzing the signals detected by the first detection sensitivity from the fourth measurement specimen, and measure bacteria in the body fluid sample by analyzing the signals detected by the second detection sensitivity from the fourth measurement specimen.

13. The urine analyzer according to claim 1, further comprising a mode setting section for setting an operation mode from the plurality of operating modes including the urine measurement mode and the body fluid measurement mode.

* * * * *